United States Patent [19]

Nakamori et al.

[11] Patent Number: 5,449,580

[45] Date of Patent: Sep. 12, 1995

[54] ORGANIC PHOTOSENSITIVE MATERIAL FOR ELECTROPHOTOGRAPHY

[75] Inventors: Hideo Nakamori; Masashi Tanaka; Toshiyuki Fukami; Masato Katsukawa, all of Osaka, Japan

[73] Assignee: Mita Industrial Co., Ltd., Osaka, Japan

[21] Appl. No.: 128,660

[22] Filed: Sep. 30, 1993

[30] Foreign Application Priority Data

Oct. 2, 1992 [JP] Japan .................. 4-264903
Oct. 5, 1992 [JP] Japan .................. 4-265217

[51] Int. Cl.$^6$ .................. G03G 5/047; G03G 5/09
[52] U.S. Cl. .................. 430/58; 430/59; 430/83
[58] Field of Search .................. 430/58, 59, 83

[56] References Cited

U.S. PATENT DOCUMENTS

| | | | |
|---|---|---|---|
| 5,166,016 | 11/1992 | Badesha et al. | 430/58 X |
| 5,176,976 | 1/1993 | Kikuchi et al. | 430/58 |
| 5,213,923 | 5/1993 | Yokoyama et al. | 430/58 |
| 5,213,926 | 5/1993 | Hanatani et al. | 430/59 |
| 5,288,573 | 2/1994 | Hung et al. | 430/58 |
| 5,324,610 | 6/1994 | Tanaka et al. | 430/59 X |

FOREIGN PATENT DOCUMENTS

| | | |
|---|---|---|
| 0337307 | 10/1989 | European Pat. Off. . |
| 0392805 | 10/1990 | European Pat. Off. . |
| 0504794 | 9/1992 | European Pat. Off. . |
| 0506387 | 9/1992 | European Pat. Off. . |
| 0506441 | 9/1992 | European Pat. Off. . |
| 0552740 | 7/1993 | European Pat. Off. . |

OTHER PUBLICATIONS

Patent Abstracts of Japan vol. 14, No. 1(P-985) (3944) 8 Jan. 1990 & JP-A-01 253 753 (Konica) 11 Oct. 1989.
Patent Abstracts of Japan vol. 13, No. 460 (P-946) (3803) 18 Oct. 1989 & JP-A-01 179 160 (Konica) 17 Jul. 1989.

*Primary Examiner*—Roland Martin
*Attorney, Agent, or Firm*—Sherman and Shalloway

[57] ABSTRACT

Disclosed is an organic photosensitive material for electrophotography which is characterized by containing a specific diphenoquinone derivative in an organic photosensitive layer of the material. The diphenoquinone derivative is a compound represented by the following general formula:

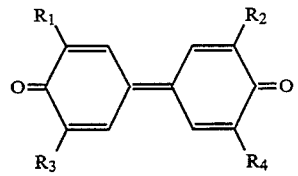

wherein $R_1$, $R_2$, $R_3$ and $R_4$ are alkyl groups, alkoxy groups, aryl groups or aralkyl groups, and at least one of $R_1$, $R_2$, $R_3$ and $R_4$ is an aryl group or an aralkyl group, and at least 2 of the remaining $R_1$, $R_2$, $R_3$ and $R_4$ are alkyl groups or alkoxy groups, the organic photosensitive material mentioned above has excellent sensitivity and residual potential.

37 Claims, No Drawings

ORGANIC PHOTOSENSITIVE MATERIAL FOR ELECTROPHOTOGRAPHY

BACKGROUND OF THE INVENTION

1. Field of the Invention

The present invention relates to an organic photosensitive material for electrophotography used for copying machines, laser printers and the like. More specifically, the invention relates to an organic photosensitive material for electrophotography containing a particular diphenoquinone derivative and having excellent sensitivity and residual potential.

2. Description of Prior Art

A source of light having a wavelength of longer than 700 nm is usually used for photosensitive materials for electrophotography that employs a digital optical system. As photosensitive materials that are sensitive in this wavelength region, there have been known organic photosensitive materials (OPCs), amorphous silicon (a-Si) and some selenium photosensitive materials. From the overall standpoint such as sensitivity and cost, however, OPCs are used in many cases.

Many organic photosensitive materials are those of the so-called function separated type, i.e., the laminated layer type in which a charge-generating layer (CGL) arid a charge-transporting layer (CTL) are laminated one upon the other. However, there have also been known organic photosensitive materials of the single layer type in which a charge-generating agent is dispersed in the medium of the charge-transporting agent.

The charge-transporting agents for the photosensitive material of this kind must have a high carrier mobility. However, the charge-transporting agents having high carrier mobility are in almost all cases are of the positive hole-transporting type. Therefore, those put into practical use are limited to those organic photosensitive materials of the negatively charged type. However, the organic photosensitive materials of the negatively charged type which utilize negatively charged corona discharge generate large amounts of ozone arousing such problems as polluting environment and deteriorating the photosensitive material. In order to prevent these problems, special systems are needed such as a particular electrifying system for preventing generation of ozone, a system for decomposing ozone that is formed, and a system for exhausting ozone in the apparatus, causing the process and the system to become complex. Moreover, the laminated layer type photosensitive material needs the photosensitive layer to be coated twice or the photosensitive layer has an interface that exists between the charge-generating layer and the charge-transporting layer and that develops interference fringes which is a problem from the optical point of view.

Among a few examples of the charge-transporting agents having electron-transporting ability, Japanese Laid-Open Patent Publication No. 206349/1989 proposes a compound having a diphenoquinone structure as a charge-transporting agent for electrophotography.

It has been said that the diphenoquinone derivatives exhibit good transporting ability but exhibit poor sensitivity when they are used for high-speed copying machines and are, hence, not yet satisfactory from the practical point of view.

SUMMARY OF THE INVENTION

The present inventors have discovered the fact that among a variety of diphenoquinone derivatives, the diphenoquinone derivatives having substituents at particular positions exhibit markedly excellent sensitivity compared with the diphenoquinone derivatives that have heretofore been known as electron-transporting agents.

That is, the object of the present invention is to provide a photosensitive material for electrophotography having high sensitivity.

Another object of the present invention is to provide a photosensitive material for electrophotography which contains a particular diphenoquinone derivative as an electron-transporting agent which can be positively charged in an image-forming apparatus, and which enables the copying speed to be increased.

According to the present invention, there is provided an organic photosensitive material for electrophotography wherein an organic photosensitive layer contains a diphenoquinone derivative represented by the following general formula (1);

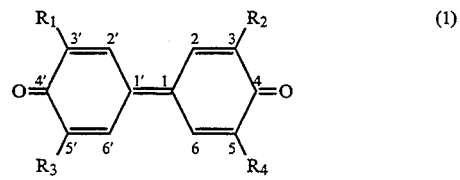

wherein $R_1$, $R_2$, $R_3$ and $R_4$ are alkyl groups, alkoxy groups, aryl groups or aralkyl groups, and at least one of $R_1$, $R_2$, $R_3$ and $R_4$ is an aryl group or an aralkyl group, and at least 2 of the remaining $R_1$, $R_2$, $R_3$ and $R_4$ are alkyl groups or alkoxy groups.

It is desired that in the above general formula (1), at least one of $R_1$, $R_2$, $R_3$ and $R_4$ is a branched chain alkyl group with 3 to 9 carbon atoms.

The most preferred example is a diphenoquinone derivative of the tri-substituted type having three kinds of substituents represented by the general formula (1) wherein $R_1$ is a tertiary alkyl group with 4 to 9 carbon atoms, $R_3$ is a phenyl group or a benzyl group, $R_2$ and $R_4$ are primary or secondary alkyl groups or alkoxy groups.

According to the present invention, furthermore, there is provided an organic photosensitive material for electrophotography having a photosensitive layer in which a charge-generating agent is dispersed in a medium that contains the charge-transporting agents, wherein at least part of the charge-transporting agents is a diphenoquinone derivative represented by the above general formula (1).

According to the present invention, there is further provided a photosensitive material for electrophotography comprising an electrically conducting substrate on which is provided a photosensitive layer that contains a positive hole-transporting agent and a diphenoquinone derivative of the above general formula (1) as an electron-transporting agent.

As the positive hole-transporting agents, the following compounds can be advantageously used:

A compound represented by the following general formula (2);

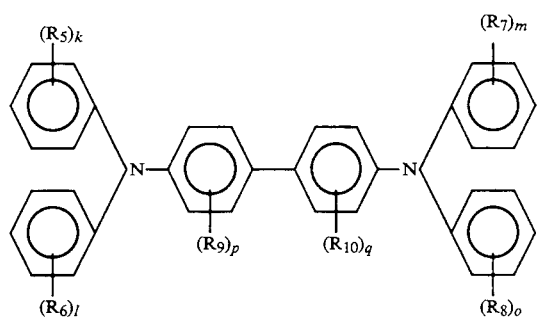

wherein $R_5$, $R_6$, $R_7$, $R_8$, $R_9$ and $R_{10}$ are alkyl groups, alkoxy groups, halogen atoms, aryl groups, nitro groups, cyano groups or alkylamino groups independently of each other, p and q are integers 0 to 4, and k, l, m and o are integers of 0 to 5;

a compound represented by the following general formula (3);

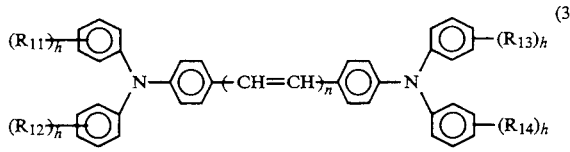

wherein $R_{11}$, $R_{12}$, $R_{13}$ and $R_{14}$ are hydrogen atoms, alkyl groups or alkoxy groups, and n and h are integers of 1 to 3;

a compound represented by the following general formula (4);

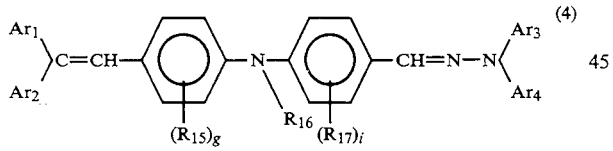

wherein $R_{15}$ and $R_{17}$ are alkyl groups, alkoxy groups or halogen atoms, g and i are integers of 0 to 4, $R_{16}$ is a hydrogen atom, an alkyl group which may have a substituent, an aralkyl group, an aryl group, or a heterocyclic group, $Ar_1$ and $Ar_2$ are alkyl groups, aralkyl groups aryl groups or heterocyclic groups which may have substituents but $Ar_1$ and $Ar_2$ may be coupled together to form a ring except when $Ar_1$ and $Ar_2$ are hydrogen atoms simultaneously, and $Ar_3$ and $Ar_4$ are alkyl groups, aralkyl groups, aryl groups or heterocyclic rings which may have substituents but $Ar_3$ and $Ar_4$ may be coupled together to form a ring;

a compound of the following general formula (5);

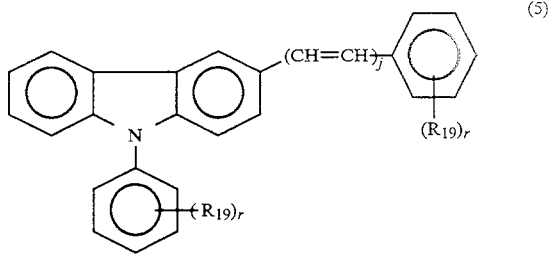

wherein $R_{15}$ and $R_{19}$ are alkyl groups or alkoxy groups, and j and r are integers of 0 to 3;

a compound represented by the following general formula (6);

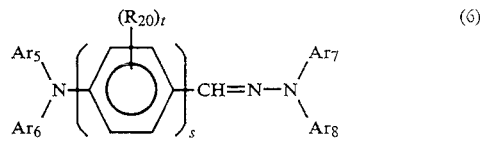

wherein $R_{20}$ is an alkyl group or an alkoxy group, $Ar_5$, $Ar_6$, $Ar_7$ and $Ar_8$ are hydrogen atoms, alkyl groups, alkoxy groups, aralkyl groups or aryl groups which may have a substituent, and s is an integer of 1 to 2, and t is an integer of 0 to 2;

a compound represented by the following general formula (7);

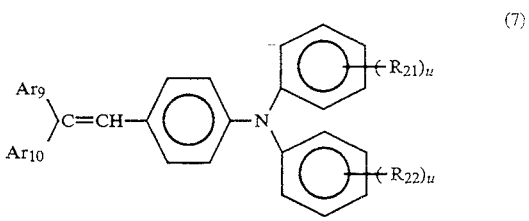

wherein $R_{21}$ and $R_{22}$ are alkyl groups or alkoxy groups, u is an integer of 0 to 2, and $Ar_9$ and $Ar_{10}$ are aryl groups which may have a substituent;

a compound represented by the following general formula (8);

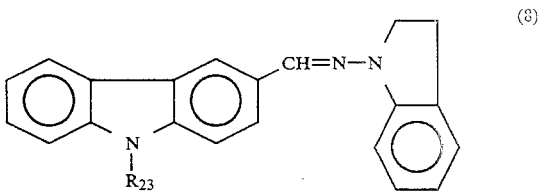

wherein $R_{23}$ is an alkyl group or an aryl group;

a compound represented by the following general formula (9);

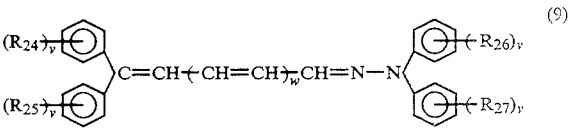

wherein $R_{24}$, $R_{25}$, $R_{26}$ and $R_{27}$ are alkyl groups or alkoxy groups and v and w are integers of 0 to 3;

a compound of the following general formula (10);

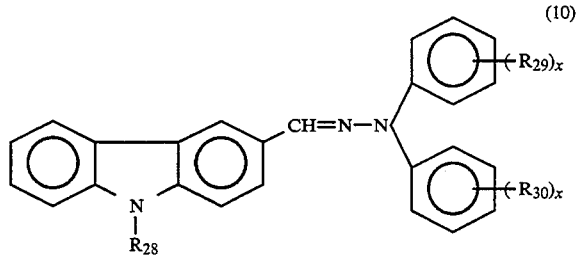
(10)

wherein $R_{28}$ and alkyl group or an aryl group, $R_{29}$ and $R_{30}$ are alkyl groups or alkoxy groups independently from each other, and x is an integer of 0 to 3; and a compound represented by the following general formula (11);

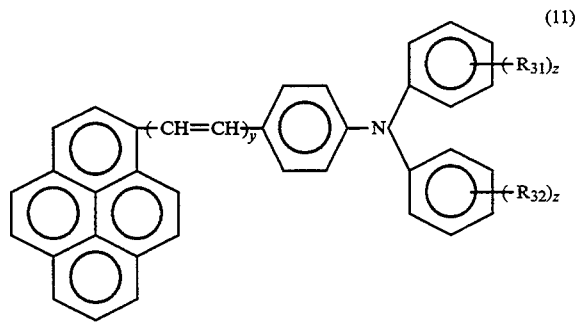
(11)

wherein $R_{31}$ and $R_{32}$ are alkyl groups or alkoxy groups, and y and z are integers of 0 to 3.

The present invention is based on a discovery that a diphenoquinone derivative having structure represented by the above general formula (1) exhibits markedly improved sensitivity and residual potential while maintaining charging property and repetitive property which are nearly equivalent to those of the diphenoquinone derivatives that have been known as electron-transporting agents.

As a diphenoquinone derivative that easily dissolves in a solvent, exhibits good compatibility to the binder resin and has the most excellent electron-transporting property, there has been known a 3,5-dimethyl-3',5'-ditertbutyl-4,4'-diphenoquinone (DMDB) of the following formula (a),

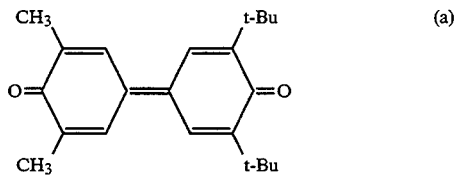
(a)

Among the diphenoquinone derivatives, the DMDB has high charging property and excellent sensitivity, but needs be improved for its sensitivity when it is used for high-speed copying machines, and is not hence still satisfactory from the practical point of view.

When a diphenoquinone derivative of the structure represented by the above general formula (1) is used in accordance with the present invention, on the other hand, it becomes possible to markedly improve the sensitivity and residual potential while maintaining the electrifying property and repetitive property at the same levels as those of the DMDB (see Examples appearing later).

The fact that the diphenoquinone derivative used in the present invention exhibits the above-mentioned improvements was found as phenomena through extensive experiments. It is presumed that the derivative has low symmetry and, hence, permits associativeness or aggregating property to be formed less in the photosensitive layer, enabling, therefore, the diphenoquinone molecules to be effectively distributed in the same volume which is advantageous for the electrons to be hopping-conducted.

The diphenoquinone derivative of the present invention should be used in combination with positive hole-transporting agents and, particularly, in combination with those positive hole-transporting agents of the general formulas (2) to (11).

In general, even when charge-transporting materials having high charge-transporting abilities are used in combination together, good electrophotographic properties are not necessarily obtained. In a system in which the positive hole-transporting material and the electron-transporting material exist together as the charge-transporting material, attention must be given to the formation of a charge-moving complex. That is, when a charge-moving complex is formed, positive holes and electrons are bonded together again, and the movement of the electric charge decreases as a whole. Moreover, when the energy gap between HOMO of the positive hole-transporting material and LUMO of the electron-transporting material is in agreement with the wavelength energy of the main exposure light and of the light for removing electricity, the light is absorbed by the charge-moving complex and the charge-generating efficiency decreases drastically.

The present inventors have have selected a compound represented by the above general formula (1) as a particular electron-transporting material and compounds represented by the above general formulas (2) to (11) as particular positive hole-transporting materials, in order to improve sensitivity, repetitive property and residual potential as will be comprehended from the comparison of Examples with Comparative Examples appearing later.

Inconvenience such as fogging does not take place even without increasing the output of the exposure lamp that is fitted as a standard lamp to the copying machine, contributing to extending the life of the exposure lamp and decreasing the consumption of electric power.

DETAILED DESCRIPTION OF THE PREFERRED EMBODIMENT (Electron-transporting agent)

In the diphenoquinone derivative of the general formula (1) used in the present invention, examples of the alkyl group include a primary alkyl group having up to 9 carbon atoms such as a methyl group, an ethyl group, an n-propyl group, an n-butyl group, an n-pentyl group, an n-hexyl group arid a 2-ethylhexyl group; a secondary alkyl group with 3 to 9 carbon atoms such as an isopropyl group and a sec-butyl group; or an alkyl group with 4 to 9 carbon atoms such as a tert-butyl group, an α, α, γ, γ-tetramethylbutyl group, and the like.

Examples of the alkoxy group include a methoxy group, an ethoxy group, a propoxy group, a butoxy group, a t-butoxy group, a hexyloxy group, and a 2-ethylhexyl, group. Among them, the methoxy group and ethoxy group are favorably used.

Examples of the aryl group include a phenyl group, an o-terphenyl group, a naphthyl group, a tolyl group, an ethylphenyl group, an anthryl group, and a phenanthryl group. Among them, the aryl group with 6 to 16 carbon atoms is preferably used.

Examples of the aralkyl group include those having 7 to 11 carbon atoms such as a benzyl group, a phenethyl group, and a cumyl group.

Examples of the substituent that may be substituted for the above groups include a halogen atom, an amino group, a hydroxyl group, a carboxyl group which may be esterified, a cyano group, an alkyl group with 1 to 6 carbon atoms, and an alkenyl group with 2 to 6 carbon atoms that may have an aryl group.

In the present invention, a diphenoquinone derivative is preferably used having three kinds of substituents which are different from each other and are represented by the following formulas (12), (13) and (14);

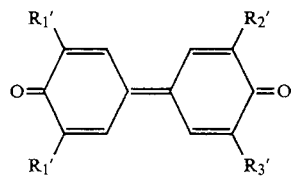

(12)

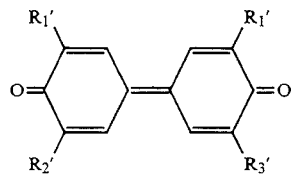

(13)

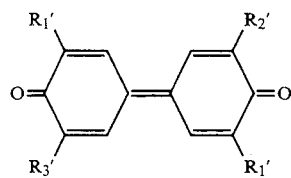

(14)

wherein $R_1'$ is an alkyl group or an alkoxy group, $R_2'$ is a secondary or tertiary alkyl group, $R_3'$ is an aryl group or an aralkyl group, and wherein $R_1'$ and $R_2'$ are different from each other.

TABLE A

| $R_1'$ | $R_2'$ | $R_3'$ |
|---|---|---|
| —CH$_3$ | —C$_2$H$_5$ | —⟨phenyl⟩ |
| —CH$_3$ | —CH(CH$_3$)$_2$ | —⟨phenyl⟩ |
| —CH$_3$ | —CH$_2$CH$_2$CH$_3$ \ CH$_3$ | —⟨phenyl⟩ |

TABLE A-continued

| $R_1'$ | $R_2'$ | $R_3'$ |
|---|---|---|
| —CH$_3$O | —C$_2$H$_5$ | —⟨phenyl⟩ |
| —CH$_3$O | —CH(CH$_3$)$_2$ | —CH$_2$—⟨phenyl⟩ |
| —CH$_3$O | —CH$_2$CH$_2$CH$_3$ \ CH$_3$ | —⟨phenyl⟩ |
| —CH(CH$_3$)$_2$ | —C(CH$_3$)$_3$ | —⟨phenyl⟩ |
| —CH(CH$_3$)$_2$ | —C(CH$_3$)$_3$ | —C(CH$_3$)$_2$—⟨phenyl⟩ |
| —C(CH$_3$)$_3$ | —C(CH$_3$)$_2$CH$_2$C(CH$_3$)$_3$ | —⟨phenyl⟩ |
| —C(CH$_3$)$_3$ | —C(CH$_3$)$_2$CH$_2$C(CH$_3$)$_3$ | —C(CH$_3$)$_2$—⟨phenyl⟩ |
| —CH$_2$CH$_2$CH$_3$ \ CH$_3$ | —C(CH$_3$)$_3$ | —⟨phenyl⟩ |
| —CH$_2$CH$_2$CH$_3$ \ CH$_3$ | —C(CH$_3$)$_3$ | —C(CH$_3$)$_2$—⟨phenyl⟩ |

The diphenoquinone derivatives represented by the above general formulas (12), (13) and (14) can be synthesized by a variety of widely known methods. For example, the diphenoquinone derivative represented by the general formula (12) can be synthesized by bringing a bi-substituted phenol represented by the following formula (i)

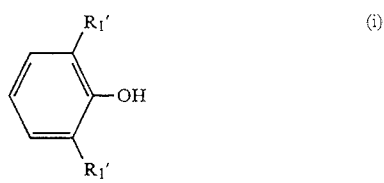

(i)

wherein $R_1'$ is as defined in the above formula (12), and a bi-substituted phenol represented by the following formula (ii)

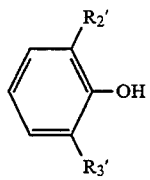

wherein R$_2'$ and R$_3'$ are as defined in the above formula (12), into contact with molecular oxygen in a polar solvent in the presence of a copper salt-tertiary amine complex catalyst.

Furthermore, the diphenoquinone derivative represented by the general formula (13) can be synthesized in the same manner as above but using bi-substituted phenols represented by the following formulas (iii) and (iv) instead of using those of the above formulas (i) and (ii),

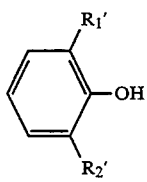

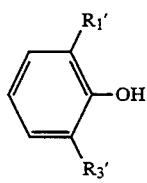

wherein R$_1'$, R$_2'$ and R$_3'$ are as defined in the above formula (13).

Further, the diphenoquinone derivative represented by the above general formula (14) can be synthesized in the same manner as described above but using bi-substituted phenols represented by the following formulas (v) and (vi) instead of using those of the above formulas (i) and (ii),

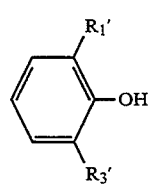

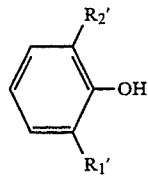

wherein R$_1'$, R$_2'$ and R$_3'$ are as defined in the above formula (14).

The diphenoquinone derivatives represented by the above general formulas (12), (13) and (14) may be used alone or being mixed together.

(Positive hole-transporting agent)

Any positive hole-transporting agents can be used such as nitrogen-containing cyclic compounds, e.g., an oxadiazole compound, a styryl-type compound, a carbazole-type compound, an organic polysilane-type compound, a pyrazoline-type compound, a hydrazone-type compound, a triphenylamine-type compound, an indole-type compound, an oxazole-type compound, an isooxazole-type compound, a thiazole-type compound, a thiadiazole-type compound, an imidazole-type compound, a pyrazole-type compound, and a triazole-type compound, as well as those of the condensed polycyclic compounds having ionization potentials of from 5.3 eV to 5.6 eV [as measured by using a photoelectron analyzer (AC-1, produced by Riken Keiki Co.) in an open atmosphere].

Though there is no particular limitation, suitable examples of the positive hole-transporting agent include:

a 1,1-bis(p-diethylaminophenyl)-4,4 diphenyl-1,3-butadiene (IP=5.32 eV, drift mobility=$7.5 \times 10^{-6}$ cm$^2$/V.sec);

an N,N'-bis(o,p-dimethylphenyl)-N,N'-diphenylbenzidine (IP=5.43 eV, drift mobility=$2.8 \times 10^{-5}$ cm$^2$/V.sec);

a 3,3'-dimethyl-N,N,N',N'-tetrakis-4-methylphenyl(1,1'-biphenyl)-4,4'-diamine (IP=5.56 eV. drift mobility=$5.1 \times 10^{-5}$ cm$^2$/V.sec);

an N-ethyl-3-carbozolylaldehyde-N,N'-diphenylhydrazone (IP=5.53 eV, drift mobility=$3.2 \times 10^{-5}$ cm$^2$/V.sec); and a 4-[N,N-bis(p-toluyl)amino]-$\beta$-phenylstilbene (IP=5.53 eV, drift mobility=$3.5 \times 10^{-5}$ cm$^2$/V.sec).

Concrete examples of the compound represented by the general formula (2) include those of Nos. A1 to A15 in Table B. In Table B, symbol "3-CH$_3$" indicates that a methyl group is bonded to the third position of the phenyl group, and "3,5-CH$_3$" indicates that methyl groups are bonded to the third position and fifth position of the phenyl group.

TABLE B

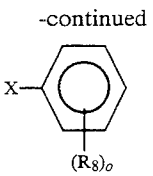

| No. | $R_5$ | $R_6$ | $R_7$ | $R_8$ | $R_9$ | $R_{10}$ |
|---|---|---|---|---|---|---|
| A1 | 3-$CH_3$ | H | H | 3-$CH_3$ | H | H |
| A2 | 3,5-$CH_3$ | H | H | 3,5-$CH_3$ | H | H |
| A3 | 2,4-$CH_3$ | H | H | 2,4-$CH_3$ | H | H |
| A4 | 4-$CH_3$ | 4-$CH_3$ | 4-$CH_3$ | 4-$CH_3$ | H | H |
| A5 | 4-$CH_3$ | 4-$CH_3$ | 4-$CH_3$ | 4-$CH_3$ | 2-$CH_3$ | 2-$CH_3$ |
| A6 | H | H | H | H | 3-$CH_3$ | 3-$CH_3$ |
| A7 | 3-$OCH_3$ | H | H | 3-$OCH_3$ | H | H |
| A8 | 2-Cl | H | H | 2-Cl | H | H |
| A9 | 4-$CH_3$ | 4-$CH_3$ | 4-$CH_3$ | 4-$CH_3$ | 3-$CH_3$ | 3-$CH_3$ |
| A10 | 2-CN | H | H | 2-CN | H | H |
| A11 | H | H | H | H | 3-$C_2H_5$ | 3-$C_2H_5$ |
| A12 | 3-$NO_2$ | H | H | 3-$NO_2$ | H | H |
| A13 | 4-$CH_3$ | 4-$CH_3$ | 4-$CH_3$ | 4-$CH_3$ | 3-$C_2H_5$ | 3-$C_2H_5$ |
| A14 | H | 4-C$_6$H$_5$ | H | 4-C$_6$H$_5$ | H | H |
| A15 | H | 4-$NC_2H_5$ | H | 4-$NC_2H_5$ | H | H |

The compound (2) can be synthesized by a variety of methods and can be synthesized by, for example, reacting a compound represented by the following general formula (15) with compounds represented by the general formulas (16) to (19) either simultaneously or successively.

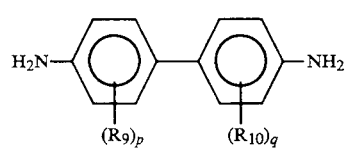

(15)

(16)

(17)

(18)

(19)

wherein $R_5$, $R_6$, $R_7$, $R_8$, $R_9$ and $R_{10}$ are alkyl groups, alkoxy groups, halogen atoms, aryl groups, nitro groups, cyano groups or alkylamino groups independently of each other, p and q are integers of 0 to 4, k, l, m and o are integers of 0 to 5, and X is a halogen atom.

Among the positive hole-transporting agents of the general formulas (2) to (11) preferably used for the present invention, the alkyl groups, alkoxy groups and aryl groups corresponding to $R_5$, $R_6$, $R_7$, $R_8$, $R_9$ and $R_{10}$ are those defined in the aforementioned general formula (1).

Examples of the halogen atom include chlorine, iodine, bromine and fluorine.

Examples of the alkylamino group include a methylamino group, a dimethylamino group, an ethylamino group a diethylamino group, a propylamino group, an isopropylamino group, a butylamino group, an isobutylamino group, a t-butylamino group, a pentylamino group and a hexylamino group.

The reaction of the compound represented by the general formula (15) with the compounds represented by the general formulas (16) to (19) is usually carried in an organic solvent. Any solvent can be used provided it does not adversely affect the reaction, such as organic solvents, e.g., a nitrobenzene, a dichlorobenzene, a quinoline, an N,N-dimethylformamide, an N-methyipyrrolidone and a dimethylsulfoxide. The reaction is usually carried out in the presence of a catalyst such as a copper powder, copper oxide or copper halide, or a basic substance such as sodium hydroxide or potassium hydrogencarbonate at a temperature of 150° to 250° C.

After the reaction, the reaction mixture is condensed, recrystallized, extracted with a solvent, and is easily isolated and purified through a customary means such as column chromatography.

In the positive hole-transporting material of the general formula (3), the alkyl groups and alkoxy groups corresponding to $R_{11}$, $R_{12}$, $R_{13}$ and $R_{14}$ are those as defined in the above general formula (1).

In the compound of the general formula (4), the alkyl groups, alkoxy groups and halogen atoms corresponding to $R_{15}$ and $R_{17}$ may be those defined in the general formula (2), and the alkyl groups and aryl groups corresponding to $R_{16}$ may be those defined in the general formula (1). Examples of the aralkyl groups include a benzyl group, a benzhydryl group, a trityl group and a phenethyl group. Examples of the heterocyclic ring group include a thienyl group, a pyrrolyl group, a pyrrolidinyl group, an oxazoiyl group, an isooxazolyl group, a thiazolyl group, an isothiazolyl group, an imidazolyl group, a 2H-imidazolyl group, a pyrazolyl group, a triazolyl group a tetrazolyl group, a pyranyl group, a pyridyl group a piperidyl group, a piperidino group, a 3-morpholinyl group, a morpholino group and a thiazolyl group. The alkyl group, aryl group, aralkyl group and heterocyclic ring group may have a substituent, respectively. Examples of the substituent include a halogen atom, an alkyl group, an alkoxy group, cyano group and the like.

The alkyl groups, aryl groups, aralkyl groups, heterocyclic groups corresponding to $Ar_1$, $Ar_2$, $Ar_3$ and $Ar_4$ and substituents which may be possessed by them may be those as defined by $R_{16}$ above. Examples of the ring formed by $Ar_1$ and $Ar_2$ which are bonded to the neighboring carbons may be a fluorenyl group and a xanthenyl group. Examples of the ring formed by $Ar_3$ and $Ar_4$ which are bonded to the neighboring bors may be an indolyl group, a 1H-indazolyl group, a benzimidazolyl group, a benztriazolyl group, and a carbazolyl group.

Examples of the compound represented by the general formula (4) include the following in addition to those described later.

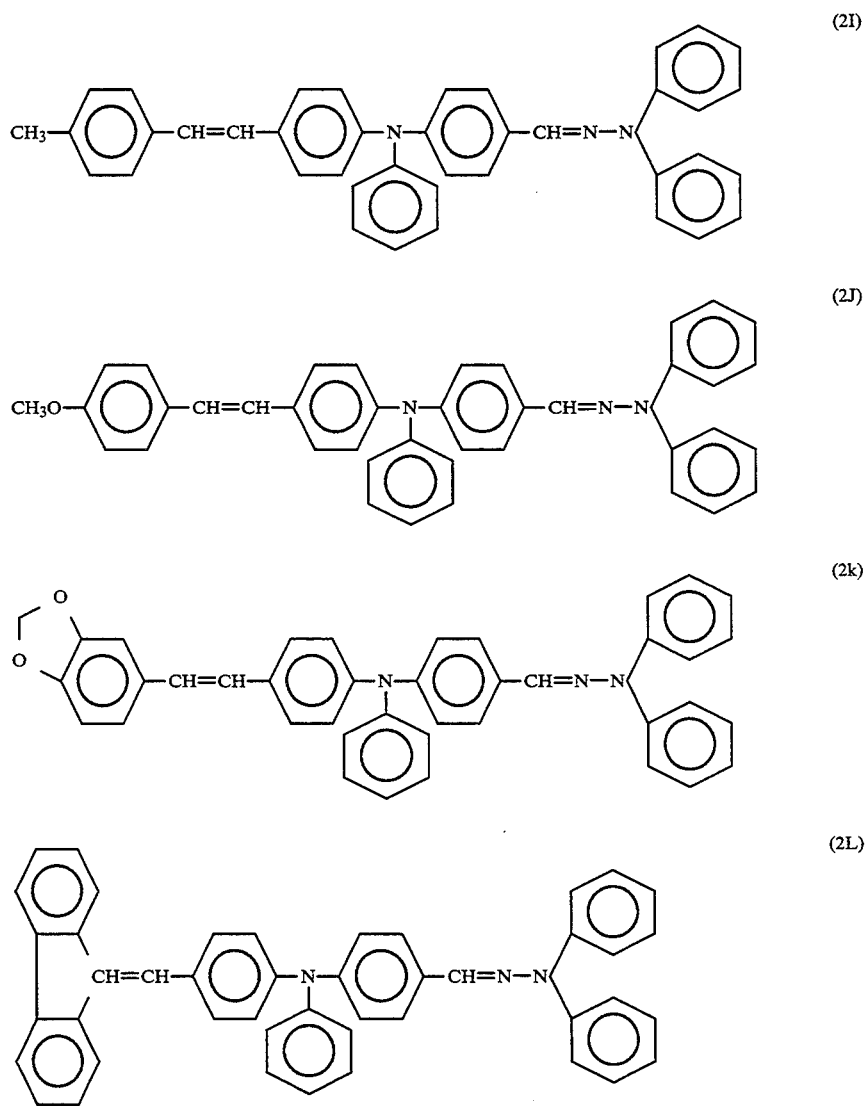

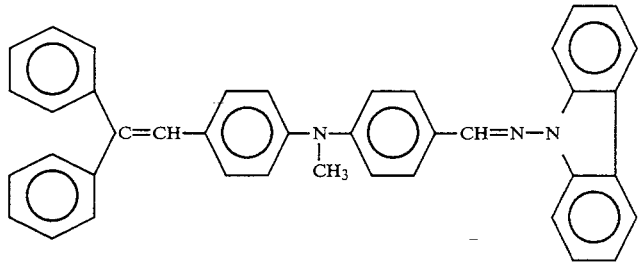 (2M)
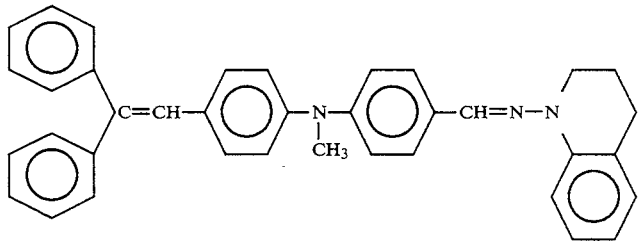 (2N)
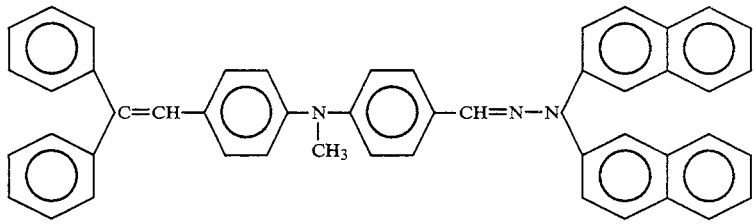 (2P)
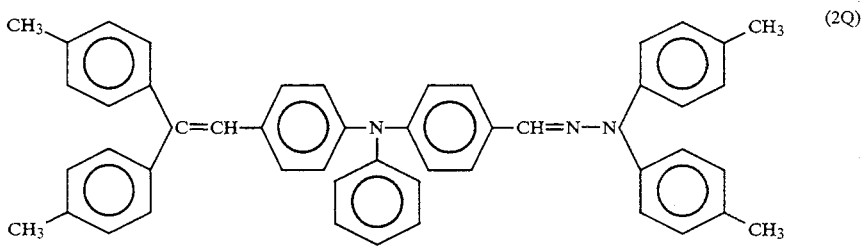 (2Q)
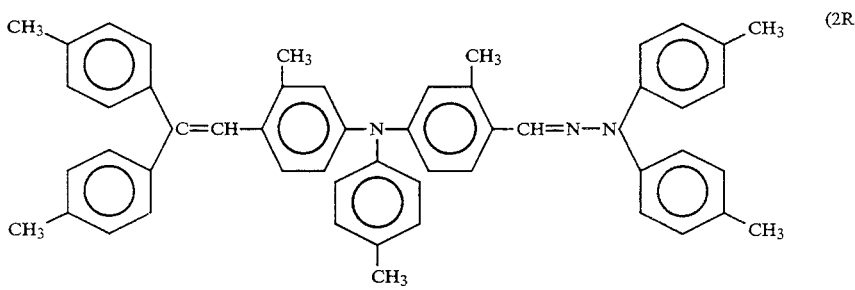 (2R)
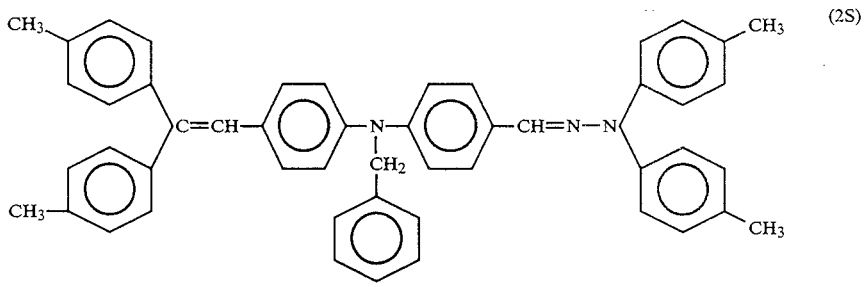 (2S)
The compounds of the formula (4) can be synthesized by a variety of known methods.
In the compound represented by the general formula (5), the alkyl groups or alkoxy groups corresponding to $R_{18}$ and $R_{19}$ are those defined by the above general formula (1). This compound is synthesized by a method known per se.

In the positive hole-transporting material represented by the above general formula (6), the alkyl group and alkoxy group corresponding to $R_{20}$ may be those defined in the general formula (1).

The alkyl groups, alkoxy groups, and aryl groups corresponding to $Ar_5$ to $Ar_8$ are those defined in the general formula (1). Examples of the aralkyl group include a benzyl group, a benzhydryl group, a trityl group and a phenethyl group.

This compound is synthesized by a method which is known per se.

In the positive hole-transporting material represented by the above general formula (7), the alkyl group and alkoxy group corresponding to $R_{21}$ and $R_{22}$ or the aryl groups corresponding to $Ar_9$ and $Ar_{10}$ are those defined by the above general formula (1). Examples of the substituent include a halogen atom, an alkyl group, an alkoxy group and a cyano group. The compound (7) is synthesized by a method known per se.

In the positive hole-transporting material represented by the above general formula (8), the alkyl group and aryl group corresponding to $R_{23}$ are those as defined in the above general formula (1). The compound (8) is synthesized by a method known per se.

In the positive hole-transporting material represented by the above general formula (9), the alkyl groups and alkoxy groups corresponding to $R_{24}$, $R_{25}$, $R_{26}$ and $R_{27}$ are those defined by the above general formula (1). The compound (9) is synthesized by a method known per se.

In the positive hole-transporting material represented by the above general formula (10), the alkyl groups and aryl groups corresponding to $R_{28}$ and the alkyl groups and alkoxy groups corresponding to $R_{29}$ and $R_{30}$ are those as defined in the above general formula (1). This compound is synthesized by a method known per se.

In the positive hole-transporting material represented by the above general formula (11), the alkyl groups and alkoxy groups corresponding to $R_{31}$ and $R_{32}$ are those as defined by the above general formula (1). This compound is synthesized by a method which is known per se.

The compounds represented by the above general formulas (1) and (2) to (11) which are the charge-transporting materials can be used in combination with any other widely known charge-transporting materials. As the widely known charge-transporting materials, there can be used a variety of electron-attracting compounds and electron-donating compounds.

Examples of the electron-attracting compound include diphenoquinone derivatives such as a 2,6-dimethyl-2',6'-ditert-dibutyldiphenoquinone and the like, a malononitrile, a thiopyrane-type compound, a tetracyanoethylene, a 2,4,8-trinitrothioxyxanthone, 3,4,5,7-tetranitro-9-fluorenone, a dinitrobenzene, a dinitroanthracene, a dinitroacridine, a nitroanthraquinone, a dinitroanthraquinone, a succinic anhydride, a maleic anhydride, and dibromomaleic anhydride.

Examples of the electron-donating compound include an oxadiazole-type compound such as a 2,5-di(4-methylaminophenyl) and a 1,3,4-oxadiazole, a styryl-type compound such as a 9-(4-diethylaminostyryl)anthracene, a carbazole-type compound such as a polyvinyl carbazole, a pyrazoline-type compound such as a 1-phenyl-3-(p-dimethylaminophenyl)pyrazoline, nitrogen-containing cyclic compounds such as a hydrazone-type compound, a triphenylaminoe-type compound, an indole-type compound, an oxazole-type compound, an isooxazole-type compound, a thiazole-type compound, a thiadiazole-type compound, an imidazole-type compound, a pyrazole-type compound and a triazole-type compound, as well as condensed polycyclic compounds.

The charge-transporting materials are used in one kind or being mixed in two or more kinds. The binder resin needs not be necessarily used when there is used a charge-transporting material having film-forming property such as polyvinyl carbazole or the like.

(Charge-generating material)

Any widely known charge-generating material can be used such as selenium, selenium-tellurium, selenium-arsenic, amorphous silicon, a pyrilium salt, an azo-type pigment, a perylene-type pigment, an anthanthrone-type pigment, a phthalocyanine-type pigment, an indigo-type pigment, a triphenylmethane-type pigment, a threne-type pigment, a toluidine-type pigment, a pyrazoline-type pigment, a quinacridone-type pigment and a pyrrolopyrrole-type pigment. Preferred examples include a metal-free phthalocyanine, a copper phthalocyanine, an oxotitanyl phthalocyanine and the like, and those materials which exhibit ionization potentials of from 5.3 eV to 5.6 eV [as measured by a photoelectron analyzer (AC-1, produced by Riken Keiki Co.) in an open air] are preferred. Particularly preferred examples are as follows:

X-type metal-free phthalocyanine (IP=5.38 eV)
β-type metal-free phthalocyanine (IP=5.32 eV)
Oxotitanyl phthalocyanine (IP=5.32 eV)
1,4-dithioketo-3,6-diphenyl-pyrrolo-(3,4-C) pyrrolopyrrole (IP=5.46 eV)
N,N-bis(3',5'-dimethylphenyl)perylene-3,4,9,10-tetracarboxyldiimide (IP=5.60 eV)

(Binder resin)

A variety of binder resins can be used. Examples include thermoplastic resins such as a styrene-type polymer, a styrene-butadiene copolymer, a styrene-acrylonitrile copolymer, a styrene-maleic acid copolymer, an acrylic copolymer, a styrene-acrylic acid copolymer, a polyethylene, an ethylene-vinyl acetate copolymer, a chlorinated polyethylene, a polyvinyl chloride, a polypropylene, a vinyl chloride-vinyl acetate copolymer, a polyesteralkyd resin, a polyamide, a polyurethane, a polycarbonate, a polyacrylate, a polysulfone, a diaryl phthalate resin, a ketone resin, a polyvinyl butylal resin, a polyether resin, and a polyester resin, as well as a silicone resin, an epoxy resin, a phenol resin, a urea resin, a melamine resin and other crosslinking thermosetting resins, and photocuring resins such as an epoxy acrylate, an urethane-acrylate and the like. The binder resins can be used in one kind or in two or more kinds being mixed together.

(Electrically conducting substrate)

A variety of materials having electrically conducting property can be used as an electrically conducting substrate for forming the photosensitive layer, such as simple metals, e.g., aluminum, copper, tin, platinum, silver, vanadium, molybdenum, chromium, cadmium, titanium, nickel, palladium, indium, a stainless steel and a brass, as well as a plastic material on which the above metals are vaporized or laminated, and a glass coated with aluminum iodide, tin oxide, indium oxide or the like.

The electrically conducting substrate may be either in the form of a sheet or a drum provided the surface itself has electrically conducting property or the surface of the substrate has electrically conducting property. It is desired that the electrically conducting substrate exhibits sufficiently large mechanical strength when it is being used.

(Additive)

The organic photosensitive layer may contain deterioration-preventing agents such as a sensitizer, a fluorene-type compound, an antioxidant and an ultraviolet-ray absorbing agent, as well as a plasticizer.

Preferred examples of the antioxidant are as follows:

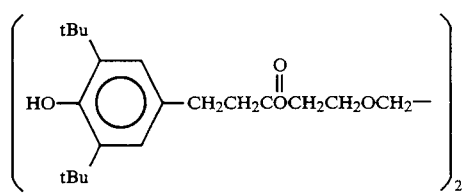 (10A)

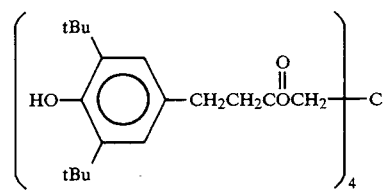 (10B)

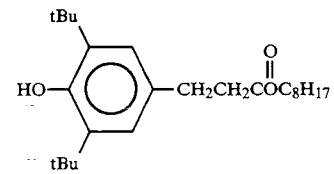 (10C)

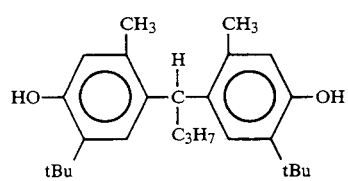 (10D)

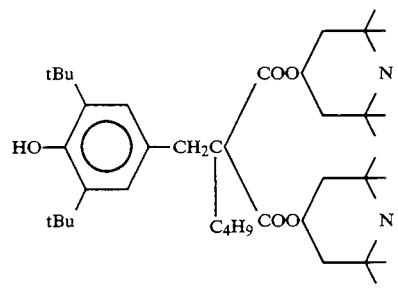 (10E)

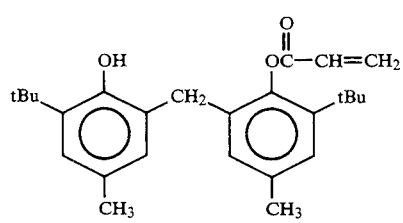 (10F)

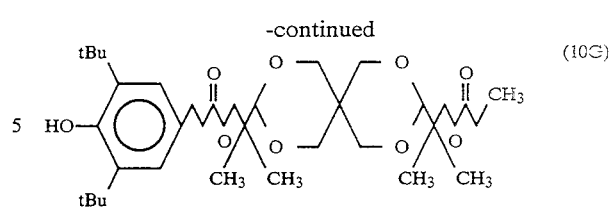 (10G)

It was found that the durability of the photosensitive layer can be strikingly improved without adversely affecting the electrophotographic properties if the above steric hindrance phenol-type antioxidant is blended in an amount of from 0.1 to 50% by weight per the whole solid content.

In order to improve the sensitivity of the charge-generating layer, furthermore, a known sensitizer such as terphenyl, halonaphthoquinones or acenaphthylene may be used together with the charge-generating material.

(Constitution of the photosensitive material)

The photosensitive material of the present invention can be adapted to the photosensitive layer of either the single layer type or the laminated layer type. However, the electron-transporting agent represented by the above general formula (1) exhibits its effects distinguished particularly in the single layer type photosensitive layer in which the charge-generating agent, positive-hole transporting agent and electron-transporting agent are contained in the same layer. It can therefore be said that the present invention is better adapted to the photosensitive material for electrophotography having a photosensitive layer of the single layer type.

In order to obtain a photosensitive material of the single layer type, the photosensitive layer containing a charge-generating material, a compound of the above general formula (1) which is an electron-transporting material and, as required, compounds represented by the above formulas (2) to (11) which are positive hole-transporting materials, and a binder resin, should be formed on the electrically conducting substrate by such means as coating or the like.

That is, a charge image in the single layer system is formed based on the principle in that electrons are injected into the electron-transporting material when a charge (positive holes, electrons) is generated in the charge-generating material due to exposure, positive holes are injected into the positive-hole transporting material, and the thus injected charge (positive holes, electrons) is exchanged in the transporting materials without being trapped and is finally transported to the surface of the photosensitive layer or to the surface of the electrically conducting substrate.

That is, in the above-mentioned photosensitive material of the single layer type, trapping of the electric charge is suppressed contributing to improving sensitivity and further enabling the photosensitive material to be electrified into both polarities to find a wide range of applications. Moreover, the photosensitive material of the single layer type does not require the photosensitive layer to be applied twice, and contributes to increasing productivity.

The photosensitive material of the laminated layer type can be obtained by forming a charge-generating layer containing a charge-generating material on the electrically conducting substrate by such means as vaporization or coating, and by forming on the charge-generating layer a charge-transporting layer which contains a compound represented by the general formula (1) which is an electron-transporting material, compounds represented by the above general formulas (2) to (11) which are positive hole-transporting materials, and a binder resin. It is also allowable to form a charge-transporting layer on the electrically conducting substrate and then form a charge-generating layer thereon.

The above-mentioned photosensitive material of the laminated layer type can be charged into both polarities to find a wide range of applications.

It is further allowable to form a positive hole-transporting layer containing a binder resin and compounds represented by the general formulas (2) to (11) which are the positive hole-transporting materials on the electrically conducting substrate, form a charge-generating layer containing the charge-generating material on the positive hole-transporting layer by such means as vaporization or coating, and form an electron-transporting layer containing a binder resin and a compound represented by the general formula (1) which is the electron-transporting material on the charge-generating layer.

The photosensitive material of the above-mentioned laminated layer type is of the positively charged type. It is allowable to form the electron-transporting layer on the electrically conducting substrate and then form the charge-generating layer and the positive hole-transporting layer.

The photosensitive material of the above-mentioned laminated layer type is of the negatively charged type.

It is further allowable to provide a protection layer on the organic photosensitive layer and to provide an intermediate layer between the organic photosensitive layer and the electrically conducting substrate.

When formed in a single layer, the organic photosensitive layer should have a thickness of from 10 to 50 $\mu$m and, more preferably, from 15 to 30 $\mu$m.

It is desired that the charge-generating material is contained in an amount of from 10 to 20 parts by weight and, more preferably, from 1 to 10 parts by weight per 100 parts by weight of the binder resin in the organic photosensitive layer. When the content of the charge-generating material is smaller than 1 part by weight, the obtained photosensitive material exhibits small charge-generating ability. When the content of the charge-generating material is greater than 20 parts by weight, on the other hand, the obtained photosensitive material may lose abrasion resistance.

It is desired that the electron-transporting material represented by the above general formula (1) is contained in an amount of from 10 to 100 parts by weight and, more preferably, from 20 to 70 parts by weight per 100 parts by weight of the binder resin in the organic photosensitive layer. When the content of the electron-transporting material is smaller than 10 parts by weight, the obtained photosensitive material exhibits poor sensitivity and repetitive property. When the content of the electron-transporting material is greater than 100 parts by weight, on the other hand, the obtained photosensitive material may lose abrasion resistance.

it is desired that the positive hole-transporting materials represented by the above general formulas (2) to (11) are contained in amounts of from 10 to 100 parts by weight and, more preferably, from 20 to 70 parts by weight per 100 parts by weight of the binder resin in the organic photosensitive layer. When the content of the positive hole-transporting materials is smaller than 10 parts by weight, the obtained photosensitive material loses sensitivity. When the content of the positive hole-transporting materials becomes greater than 100 parts by weight, on the other hand, the obtained photosensitive material may lose abrasion resistance.

It is desired that the electron-transporting material represented by the above general formula (1) is contained in an amount of from 20 to 80% by weight and, particularly, in an amount of 30 to 70% by weight in the charge-transporting material. When the content of the electron-transporting material in the charge-transporting material is smaller than 20% by weight, the obtained photosensitive material exhibits poor sensitivity and repetitive property. When the content of the electron-transporting material is greater than 80% by weight, on the other hand, the obtained photosensitive material exhibits poor sensitivity.

When the organic photosensitive layer comprises the charge-generating layer and the charge-transporting layer, the charge-generating layer should have a thickness of from 0.1 to 5 $\mu$m and, more preferably, from 0.5 to 2 $\mu$m. The charge-transporting layer should have a thickness of from 10 to 50 $\mu$m and, more preferably, from 15 to 30 $\mu$m.

It is desired that the charge-generating material is contained in an amount of from 50 to 500 parts by weight and, more preferably, from 100 to 300 parts by weight per 100 parts by weight of the binder resin in the charge-generating layer. When the content of the charge-generating material is smaller than 50 parts by weight, the obtained photosensitive material exhibits small charge-generating ability. When the content of the charge-generating material is greater than 500 parts by weight, on the other hand, the obtained photosensitive material may lose mechanical strength.

It is desired that the electron-transporting material represented by the above general formula (1) is contained in an amount of from 10 to 100 parts by weight and, more preferably, from 20 to 70 parts by weight per 100 parts by weight of the binder resin in the charge-transporting layer. When the content of the electron-transporting material is smaller than 10 parts by weight, the obtained photosensitive material loses sensitivity and repetitive property. When the content of the electron-transporting material is greater than 100 parts by weight, on the other hand, the obtained photosensitive material may lose abrasion resistance.

It is desired that the positive hole-transporting materials represented by the above general formulas (2) to (11) are contained in amounts of from 10 to 100 parts by weight and, more preferably, from 20 to 70 parts by weight per 100 parts by weight of the binder resin in the charge-transporting layer. When the content of the positive hole-transporting materials is smaller than 10 parts by weight, the obtained photosensitive material loses sensitivity. When the content of the positive hole-transporting materials is greater than 100 parts by weight, on the other hand, the obtained photosensitive material may lose abrasion resistance.

It is desired that the electron-transporting material represented by the above general formula (1) is contained in an amount of from 20 to 80% by weight and, particularly, from 30 to 70% by weight in the charge-transporting material. When the content of the electron-transporting material is smaller than 20% by weight in the charge-transporting material, the obtained photosensitive material loses sensitivity and repetitive property. When the content of the electron-transporting material is greater than 80% by weight, on the other hand, the obtained photosensitive material loses sensitivity.

(Preparation of photosensitive material)

When the above-mentioned layers are to be formed by the method of coating, the above-mentioned charge-generating material, charge-transporting material, binder resin and the like are dispersed and mixed together by a conventional method, such as by using a roll mill, a ball mill, an attritor, a paint shaker or an ultrasonic wave dispersing device to prepare a coating solution which is then applied and dried in a customary manner.

A variety of organic solvents can be used for preparing a coating solution. Examples include alcohols such as methanol, ethanol, isopropanol, butanol and the like; aliphatic hydrocarbons such as n-hexane, octane, cyclohexane and the like; aromatic hydrocarbons such as benzene, toluene and xylene; halogenated hydrocarbons such as dichloromethane, dichloroethane, carbon tetrachloride, chlorobenzene and the like; ethers such as dimethyl ether, diethyl ether, tetrahydrofurane, ethylene glycol dimethyl ether, diethylene glycol dimethyl ether and the like; ketones such as acetone, methyl ethyl ketone, cyclohexanone and the like; esters such as ethyl acetate, methyl acetate and the like; and dimethylformaldehyde, dimethylformamide, dimethyl sulfoxide and the like. These solvents can be used in a single kind or in two or more kinds being mixed together.

It is further allowable to use a surfactant and a levelling agent in order to improve dispersion property of the charge-transporting material and the charge-generating material and to improve smoothness on the surface of the photosensitive layer.

The invention will now be described in detail by way of Working Examples and Comparative Examples.

Synthesis 1.

Synthesis of a 3,5-diisopropyl-3'-t-butyl-5'-phenyl-4,4-diphenoquinone.

7.8 Grams of a 2,6-diisopropylphenol, 9.94 g of a 2-t-butyl-6-phenylphenol, 0.18 g of a cuprous chloride, 0.414 g of a tetramethylethylene diamine, and 100 milliliters of methanol were fed into a 500-milliliter separable flask equipped with an oxygen gas introduction pipe, a waste gas exhaust pipe and a stirrer. The reaction was carried out with vigorous stirring while feeding a pure oxygen gas into the gas phase in the flask. After the reaction, the precipitated crystals were separated by filtration, washed with water and dried. The crystals were then isolated using a column chromatography filled with silica gel to obtain an object material represented by the following general formula (c). The amount of the object material was 4.9 g (yield, 27%).

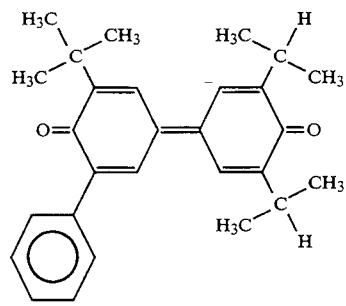

Synthesis 2.

Synthesis of a 3,5-diisopropyl-3'-($\alpha,\alpha,\gamma,\gamma$-tetramethylbutyl)-5'-phenyl-4,4'-diphenoquinone.

The reaction was carried out in the same manner as in the above Synthesis 1 with the exception of using a 2,6-diisopropylphenol and a 2-($\alpha,\alpha,\gamma,\gamma$-tetramethylbutyl)-6-phenylphenol as bi-substituted phenols which are starting materials, in order to obtain an object material represented by the following general formula (d). The amount of the object material was 6.4 g (yield, 32%).

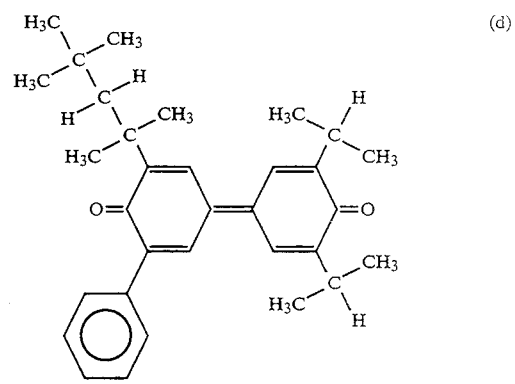

Synthesis 3.

Synthesis of a 3,5-di(secondary butyl)-3'-t-butyl-5'-phenyl-4,4'-diphenoquinone.

The reaction was carried out in the same manner as in Synthesis 1 with the exception of using a 2,6-di(secondary butyl)phenol and a 2-t-butyl-6-phenylphenol as bi-substituted phenols which are starting materials, in order to obtain an object material represented by the following general formula (b),

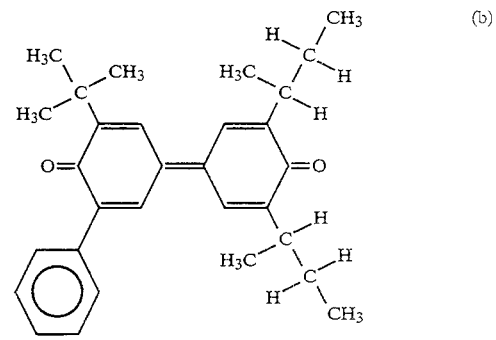

Synthesis 4.

Synthesis of a 3,5-dimethoxy-3'-($\alpha,\alpha,\gamma,\gamma$-tetramethylbutyl)-5'-phenyl-4,4'-diphenoquinone.

The reaction was carried out in the same manner as in Synthesis 1 with the exception of using a 2,6-dimethoxyphenol and a 2-phenyl-6-($\alpha,\alpha,\gamma,\gamma$-tetramethylbutyl)-phenol as bi-substituted phenols which are starting materials, in order to obtain an object material represented by the following general formula (e),

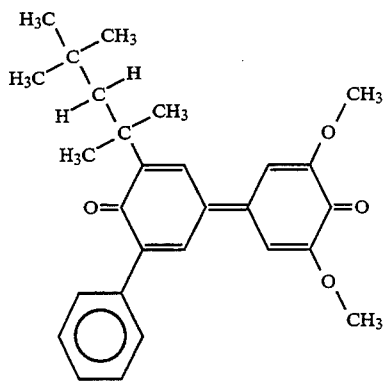

(e)

Synthesis 5.

Synthesis of a 3,5-dimethyl-3'-(secondary butyl)-5'-(α-dimethyl-benzyl) 4,4'-diphenoquinone.

The reaction was carried out in the same manner as in Synthesis 1 with the exception of using a 2,6-dimethylphenol and a 2-(α-dimethyl-benzyl)-6-(secondary butyl)-phenol as bi-substituted phenols which are starting materials, in order to obtain an object material represented by the following general formula (f),

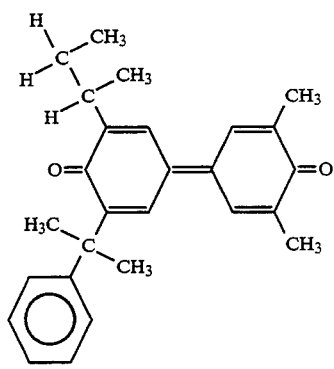

(f)

Single layer type photosensitive material for electrophotography.

Examples 1 to 36 and Comparative Examples 1 to 8

5 Parts by weight of a charge-generating agent 40 parts by weight of an electron-transporting agent, 40 parts by weight of a positive hole-transporting agent, 100 parts by weight of a polycarbonate which is a binder, and a predetermined amount of dichloromethane which is a solvent were mixed and dispersed in a ball mill to prepare a coating solution for the single layer type photosensitive layer. The coating solution was applied onto an aluminum foil using a wire bar, and was dried with the hot air heated at 100° C. for 60 minutes to obtain a single layer type photosensitive material for electrophotography having a thickness of 15 to 20 μm.

As the charge-generating agent, the following compounds I and II were used.

I: X-type metal-free phthalocyanine (IP=5.38 eV)
II: Oxotitanyl phthalocyanine (IP=5.32 eV)

As the positive hole-transporting agent, the compounds of the following general formulas (A) to (E) were used:

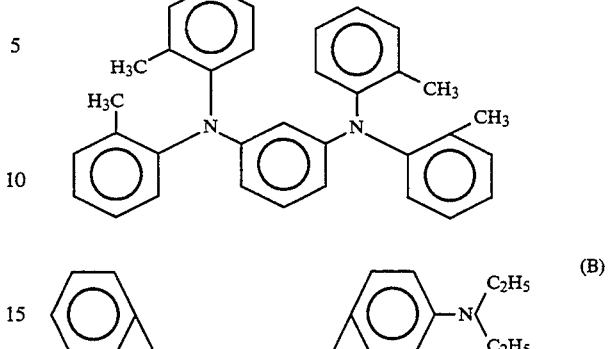
(A)

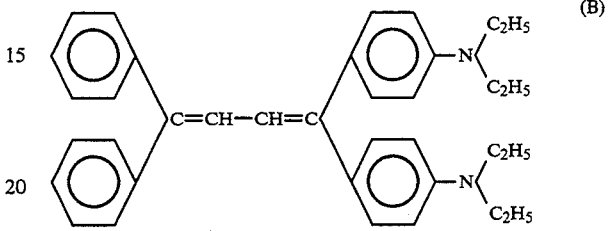
(B)

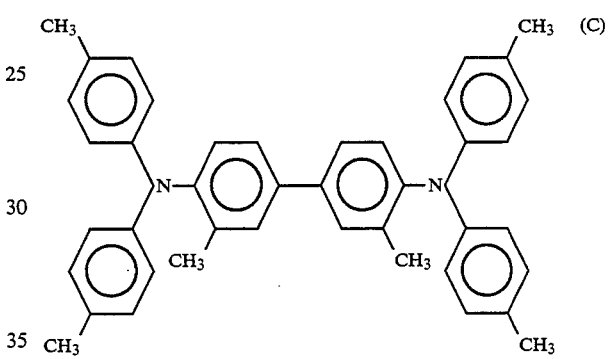
(C)

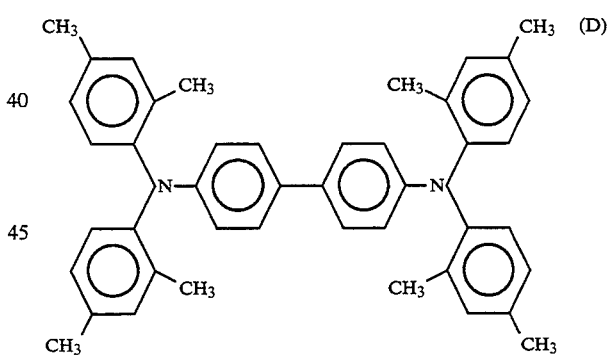
(D)

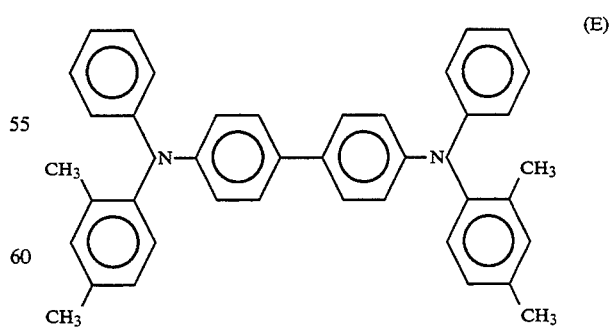
(E)

As the electron-transporting agent, the compounds of the aforementioned formulas (a) to (f) were used as concretely shown in Table 2. Laminated layer type photosensitive material for electrophotography.

Examples 37 to 57 and Comparative Examples 9 to 13

100 Parts by weight of a charge-generating agent, 100 parts by weight of a butyral resin as a binding agent and a predetermined amount of tetrahydrofurane as a solvent were mixed and dispersed in a ball mill to prepare a coating solution for the charge-generating layer. The coating solution was applied onto an aluminum foil using a wire bar and was dried with the hot air heated at 100° C. for 60 minutes to form a charge-generating layer having a thickness of 1 to 2 μm. Then, 40 parts by weight of an electron-transporting agent, 40 parts by weight of a positive hole-transporting agent, 100 parts by weight of polycarbonate as a binding agent and a predetermined amount of toluene as a solvent were mixed and dispersed in a ball mill to prepare a coating solution for the charge-transporting layer. The coating solution was applied onto the above charge-generating layer by using a wire bar and was dried with the hot air heated at 100° C. for 60 minutes to obtaina laminated layer type photosensitive material for electrophotography having a thickness of 15 to 20 μm.

The charge-generating agent, positive hole-transporting agent, and electron-transporting agent used were the same as those used for the above-mentioned single layer type photosensitive material for electrophotography as concretely shown in Table 3.

The photosensitive materials for eletrophotography of the above Examples and Comparative Examples were tested as described below to evaluate their properties.

(Electric property)

By using an electrostatic copy tester (EPA-8100 manufactured by Kawaguchi Denki Co.), voltages of ±7 KV were applied to the surfaces of the sheet-like photosensitive materials for electrophotography prepared in Examples and Comparative Examples to charge the surfaces thereof into positive or negative potential in order to measure the initial surface potential V1 (V). Thereafter, the surfaces were irradiated with light from an incandescent halogen lamp that is a source of light for exposure for 6 seconds to measure the half exposure amount (μJ/cm2). Further, after three seconds have passed from the start of the exposure, the surface potential was found as the initial residual potential V2 (V).

(Repetitive property)

The photosensitive materials for electrophotography obtained in the aforementioned Examples and Comparative Examples were stuck to an aluminum cylinder using an adhesive tape and were fitted onto an electrostatic copying machine DC-1656 (manufactured by Mira Kogyo Co.).

After the copying operation was repeated 1000 times, the surface potential $V1'$ (V) before exposure and the potential $V2'$ (V) after exposure were measured in the same manner as above, and the differences from the initial surface potential and the initial residual potential were calculated by using the following relations.

$$\Delta V1 = |V1'| - |V1|$$

$$\Delta V2 = |V2'| - |V2|$$

The results were as shown in Tables 2 and 3.

TABLE 2

| | Charge-generating agent | Hole-transporting agent | Electron-transporting agent | V1 (V) | V2 (V) | E1/2 (μJ/cm$^2$) | Repetitive property ΔV1 (V) | ΔV2 (V) |
|---|---|---|---|---|---|---|---|---|
| Example 1 | I | A | (b) | 699 | 95 | 1.8 | −18 | +19 |
| Example 2 | I | A | (c) | 704 | 99 | 1.9 | −20 | +11 |
| Example 3 | I | A | (d) | 694 | 92 | 1.8 | −15 | +21 |
| Example 4 | I | A | (e) | 704 | 98 | 1.9 | −14 | +15 |
| Example 5 | I | A | (f) | 713 | 94 | 1.8 | −17 | +18 |
| Example 6 | I | B | (b) | 713 | 98 | 1.9 | −18 | +18 |
| Example 7 | I | B | (c) | 709 | 97 | 2.0 | −19 | +15 |
| Example 8 | I | B | (d) | 712 | 94 | 1.8 | −21 | +17 |
| Example 9 | I | B | (e) | 695 | 93 | 1.8 | −15 | +13 |
| Example 10 | I | B | (f) | 708 | 99 | 1.9 | −17 | +18 |
| Example 11 | II | A | (b) | 704 | 83 | 1.7 | −22 | +22 |
| Example 12 | II | A | (c) | 687 | 86 | 1.8 | −15 | +19 |
| Example 13 | II | A | (d) | 712 | 87 | 1.7 | −13 | +17 |
| Example 14 | II | A | (e) | 717 | 82 | 1.7 | −21 | +15 |
| Example 15 | II | A | (f) | 689 | 85 | 1.8 | −14 | +20 |
| Example 16 | I | A | (b) | −715 | −103 | 2.0 | −25 | +21 |
| Example 17 | I | B | (b) | −698 | −108 | 2.0 | −21 | +19 |
| Example 18 | II | A | (b) | −711 | −99 | 2.0 | −19 | +15 |
| Example 19 | I | C | (b) | 707 | 71 | 1.6 | −11 | +8 |
| Example 20 | I | C | (c) | 693 | 65 | 1.5 | −8 | +10 |
| Example 21 | I | C | (d) | 697 | 69 | 1.6 | −10 | +8 |
| Example 22 | I | C | (e) | 721 | 68 | 1.6 | −10 | +11 |
| Example 23 | I | C | (f) | 715 | 73 | 1.7 | −9 | +9 |
| Example 24 | I | D | (b) | 707 | 67 | 1.6 | −10 | +9 |
| Example 25 | I | D | (c) | 705 | 72 | 1.7 | −9 | +11 |
| Example 26 | I | D | (d) | 721 | 71 | 1.6 | −7 | +10 |
| Example 27 | I | D | (e) | 695 | 74 | 1.7 | −12 | +10 |
| Example 28 | I | D | (f) | 713 | 70 | 1.6 | −9 | +10 |
| Example 29 | I | E | (b) | 708 | 68 | 1.6 | −10 | +8 |
| Example 30 | I | E | (c) | 695 | 66 | 1.5 | −11 | +7 |
| Example 31 | I | E | (d) | 699 | 70 | 1.6 | −9 | +8 |
| Example 32 | I | E | (e) | 724 | 69 | 1.6 | −8 | +9 |
| Example 33 | I | E | (f) | 709 | 73 | 1.7 | −9 | +9 |
| Example 34 | I | C | (b) | −710 | −81 | 1.6 | −11 | +10 |
| Example 35 | I | D | (b) | −714 | −85 | 1.7 | −9 | +9 |
| Example 36 | I | E | (b) | −714 | −84 | 1.7 | −12 | +11 |
| Comparative | I | A | (a) | 722 | 117 | 2.2 | −31 | +27 |

TABLE 2-continued

|  | Charge-generating agent | Hole-transporting agent | Electron-transporting agent | V1 (V) | V2 (V) | E1/2 ($\mu J/cm^2$) | Repetitive property $\Delta V1$ (V) | $\Delta V2$ (V) |
| --- | --- | --- | --- | --- | --- | --- | --- | --- |
| Example 1 |  |  |  |  |  |  |  |  |
| Comparative Example 2 | I | B | (a) | 711 | 122 | 2.3 | −37 | +29 |
| Comparative Example 3 | II | A | (a) | 703 | 106 | 2.1 | −33 | +30 |
| Comparative Example 4 | I | C | (a) | 702 | 95 | 1.8 | −25 | +19 |
| Comparative Example 5 | I | A | (a) | −703 | −125 | 2.3 | −28 | +27 |
| Comparative Example 6 | I | B | (a) | −696 | −131 | 2.4 | −25 | +33 |
| Comparative Example 7 | II | A | (a) | −716 | −118 | 2.2 | −29 | +28 |
| Comparative Example 8 | I | C | (a) | −707 | −115 | 2.1 | −28 | +21 |

TABLE 3

|  | Charge-generating layer | Charge-transporting layer | | | | | Repetitive property | |
| --- | --- | --- | --- | --- | --- | --- | --- | --- |
|  | Charge-generating agent | Hole-transporting agent | Electron-transporting agent | V1 (V) | V2 (V) | E1/2 ($\mu J/cm^2$) | $\Delta V1$ (V) | $\Delta V2$ (V) |
| Example 37 | I | A | (b) | 704 | 113 | 2.5 | −21 | +23 |
| Example 38 | I | A | (c) | 708 | 118 | 2.6 | −25 | +27 |
| Example 39 | I | A | (d) | 695 | 109 | 2.4 | −27 | +22 |
| Example 40 | I | A | (e) | 698 | 111 | 2.5 | −23 | +24 |
| Example 41 | I | A | (f) | 718 | 115 | 2.5 | −25 | +28 |
| Example 42 | I | B | (b) | 699 | 115 | 2.6 | −22 | +23 |
| Example 43 | I | B | (c) | 713 | 120 | 2.6 | −24 | +25 |
| Example 44 | I | B | (d) | 704 | 117 | 2.6 | −24 | +24 |
| Example 45 | I | B | (e) | 702 | 118 | 2.6 | −23 | +26 |
| Example 46 | I | B | (f) | 719 | 115 | 2.6 | −26 | +25 |
| Example 47 | II | A | (b) | 701 | 105 | 2.3 | −25 | +24 |
| Example 48 | II | A | (c) | 705 | 109 | 2.4 | −28 | +28 |
| Example 49 | II | A | (d) | 719 | 103 | 2.3 | −21 | +25 |
| Example 50 | II | A | (e) | 688 | 108 | 2.4 | −25 | +29 |
| Example 51 | II | A | (f) | 703 | 104 | 2.3 | −23 | +27 |
| Example 52 | I | A | (b) | −689 | −85 | 1.9 | −27 | +23 |
| Example 53 | I | — | (b) | 710 | 128 | 2.8 | −29 | +28 |
| Example 54 | I | — | (c) | 700 | 121 | 2.7 | −28 | +27 |
| Example 55 | I | — | (d) | 704 | 125 | 2.7 | −28 | +25 |
| Example 56 | I | — | (e) | 694 | 124 | 2.7 | −25 | +26 |
| Example 57 | I | — | (f) | 719 | 127 | 2.8 | −22 | +28 |
| Comparative Example 9 | I | A | (a) | 701 | 131 | 2.7 | −38 | +36 |
| Comparative Example 10 | I | B | (a) | 713 | 139 | 2.8 | −35 | +39 |
| Comparative Example 11 | II | A | (a) | 699 | 127 | 2.6 | −33 | +38 |
| Comparative Example 12 | I | A | (a) | −718 | −107 | 2.3 | −37 | +37 |
| Comparative Example 13 | I | — | (a) | 714 | 156 | 3.3 | −45 | +41 |

As will be obvious from Table 2, the single layer type photosensitive materials for electrophotography of Examples 1 to 36 could be charged into both positive and negative polarities, exhibited excellent sensitivity, residual potential and repetitive property, and exhibited particularly excellent sensitivity.

On the other hand, the positively electrified single layer type photosensitive materials of Comparative Examples 1 to 4 exhibited sensitivity, residual potential and repetitive property that were inferior to those of Examples 1 to 15 and 19 to 33. The negatively electrified single layer type photosensitive materials of Comparative Examples 5 to 8 exhibited sensitivity, residual potential and repetitive property that were inferior to those of Examples 16 to 18 and 34 to 36.

As will be obvious from Table 3, the laminated layer type photosensitive materials of the present invention of Examples 37 to 57 exhibited excellent sensitivity, residual potential and repetitive property.

On the other hand, the positively electrified laminated layer type photosensitive materials of Comparative Examples 9 to 11 exhibited sensitivity, residual potential and repetitive property that were inferior to those of Examples 37 to 51. The negatively charged laminated layer type photo-sensitive material of Comparative Example 12 exhibited sensitivity, residual potential and retitive property that were inferior to those of Example 52. Furthermore, the positively charged laminated layer type photosensitive material without containing positive hole-transporting agent of Comparative Example 13 exhibited sensitivity, residual potential and repetitive property that were inferior to those of Examples 53 to 57.

Examples 58 to 66 and Comparative Example 14

5 Parts by weight of a charge-generating material, 40 parts by weight of an electron-transporting material, 40 parts by weight of a positive hole-transporting material, 100 parts by weight of a polycarbonate resin as a binder resin, and a predetermined amount of dichloromethane as a solvent were mixed and dispersed in a ball mill to prepare a coating solution for the single layer type photosensitive material. The coating solution was applied onto an aluminum sheet using a wire bar and was dried with the hot air heated at 100° C. for 60 minutes to obtain a photosensitive material for electrophotography having a single layer type photosensitive layer which is 15 to 50 μm in thickness.

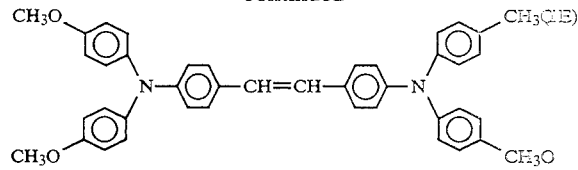

As the electron-transporting material, the compounds of the above-mentioned formulas (a) to (d) were used as concretely shown in table 4.

The photosensitive materials for electrophotography of the above Examples and Comparative Examples were tested for their electric properties and repetitive properties in the same manner as in Example 1 to evaluate their properties.

The results were as shown in Table 4.

TABLE 4

| | Hole-transporting agent | Electron-transporting agent | Photosensitivity | | | | | | Repetitive property | |
|---|---|---|---|---|---|---|---|---|---|---|
| | | | negatively charged | | | positively charged | | | | |
| | | | V1 (V) | V2 (V) | E1/2 (μJ/cm$^2$) | V1 (V) | V2 (V) | E1/2 (μJ/cm$^2$) | ΔV1 (V) | ΔV2 (V) |
| Examp. 58 | 1C | (b) | −704 | −87 | 1.7 | 707 | 73 | 1.6 | −10 | +7 |
| Examp. 59 | 1C | (c) | −701 | −86 | 1.6 | 708 | 65 | 1.5 | −8 | +10 |
| Examp. 60 | 1C | (d) | −709 | −88 | 1.7 | 693 | 73 | 1.6 | −7 | +9 |
| Examp. 61 | 1D | (b) | −714 | −85 | 1.6 | 711 | 72 | 1.6 | −9 | +8 |
| Examp. 62 | 1D | (c) | −720 | −90 | 1.7 | 703 | 79 | 1.7 | −9 | +12 |
| Examp. 63 | 1D | (d) | −724 | −84 | 1.6 | 712 | 71 | 1.6 | −7 | +9 |
| Examp. 64 | 1E | (b) | −713 | −91 | 1.8 | 722 | 72 | 1.6 | −11 | +9 |
| Examp. 65 | 1E | (c) | −706 | −87 | 1.7 | 714 | 69 | 1.5 | −11 | +12 |
| Examp. 66 | 1E | (d) | −692 | −84 | 1.6 | 699 | 73 | 1.6 | −9 | +8 |
| Comparative Examp. 14 | 1C | (a) | −720 | −105 | 2.0 | 717 | 98 | 1.9 | −19 | +18 |

As the change-generating material, the following compound (I) was used:

I: X-type metal-free phthalocyanine (IP=5.38 eV)

As the positive hole-transporting agent, the compounds off the following general formulas (1C) to (1E) were used:

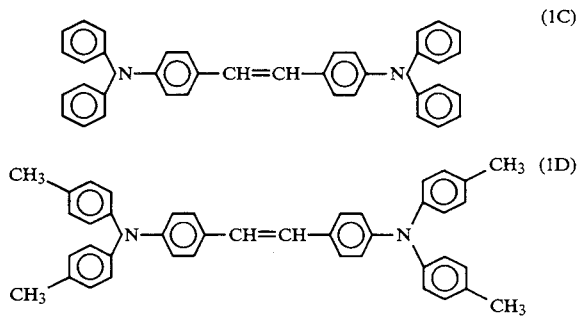

It will be understood from Table 4 that the photosensitive materials of Examples 58 to 66 are superior to the photosensitive material of Comparative Example 14 in regard to potential after exposure, half exposure amount and repetitive property.

Examples 67 to 84 and Comparative Example 15:

5 Parts by weight of a charge-generating material, 40 parts by weight of an electron-transporting material, 40 parts by weight of a positive hole-transporting material, 100 parts by weight of a polycarbonate resin as a binder resin, and a predetermined amount of dichloromethane as a solvent were mixed and dispersed in a ball mill to prepare a coating solution for the single layer type photosensitive material. The coating solution was applied onto an aluminum sheet using a wire bar and was dried with the hot air heated at 100° C. for 60 minutes to obtain a photosensitive material for electrophotography having a single layer type photosensitive layer which is 15 to 50 μm in thickness.

As the charge-generating material, the following compound (I) was used:

I: X-type metal-free phthalocyanine (IP=5.38 eV)

As the positive hole-transporting agent, the compounds of the following general formulas (2C) to (2E) were used:

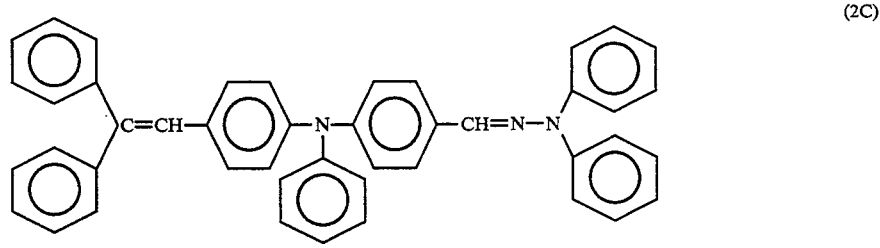
(2C)
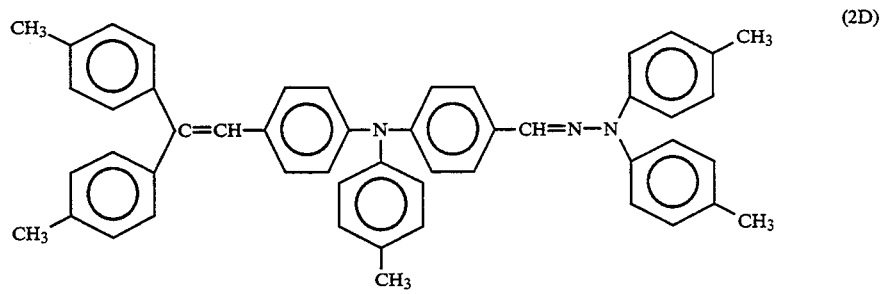
(2D)
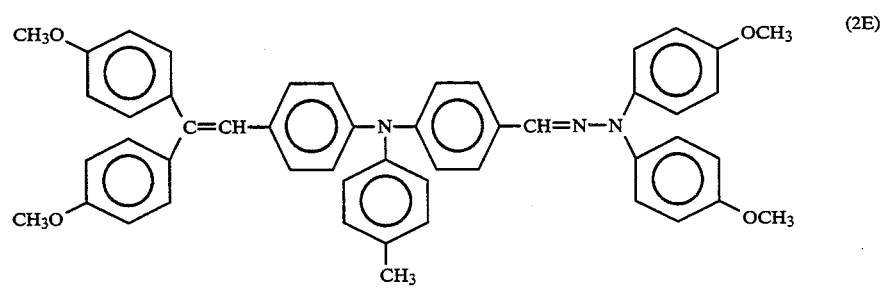
(2E)
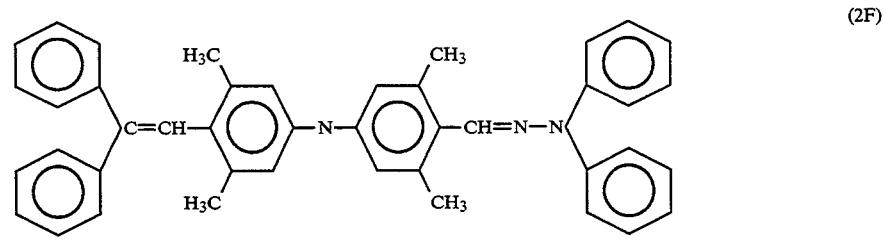
(2F)
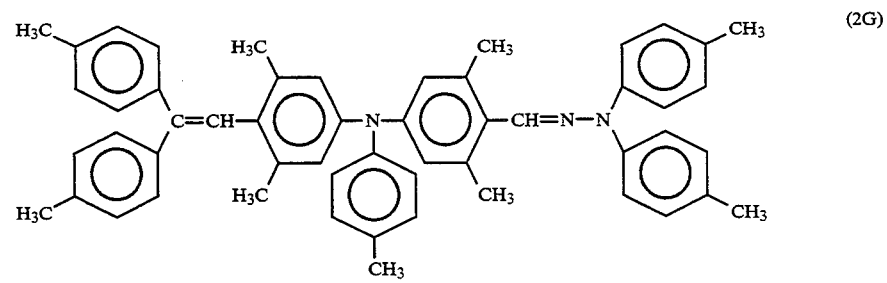
(2G)
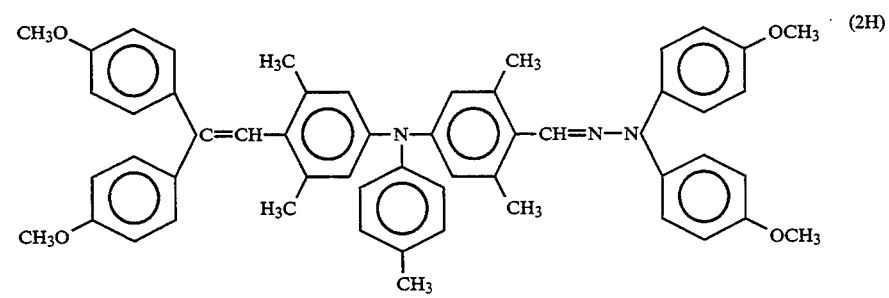
(2H)

As the electron-transporting material, the compounds of the above-mentioned formulas (a) to (d) were used as concretely shown in Table 5.

The photosensitive materials for electrophotography of the above Examples and Comparative Examples were tested for their electric properties and repetitive properties in the same manner as in Example 1 to evaluate their properties.

The results were as shown in Table 5.

TABLE 5

| | Hole-transporting agent | Electron-transporting agent | Photosensitivity | | | | | | Repetitive property | |
|---|---|---|---|---|---|---|---|---|---|---|
| | | | negatively charged | | | positively charged | | | | |
| | | | V1 (V) | V2 (V) | E1/2 (μJ/cm²) | V1 (V) | V2 (V) | E1/2 (μJ/cm²) | ΔV1 (V) | ΔV2 (V) |
| Examp. 67 | 2C | (b) | −702 | −88 | 1.8 | 712 | 72 | 1.6 | −10 | +9 |
| Examp. 68 | 2C | (c) | −696 | −85 | 1.7 | 698 | 75 | 1.7 | −7 | +11 |
| Examp. 69 | 2C | (d) | −711 | −91 | 1.8 | 694 | 72 | 1.6 | −9 | +9 |
| Examp. 70 | 2D | (b) | −715 | −88 | 1.7 | 715 | 71 | 1.6 | −9 | +10 |
| Examp. 71 | 2D | (c) | −721 | −93 | 1.9 | 709 | 68 | 1.6 | −8 | +11 |
| Examp. 72 | 2D | (d) | −705 | −91 | 1.8 | 716 | 69 | 1.6 | −11 | +8 |
| Examp. 73 | 2E | (b) | −713 | −91 | 1.8 | 708 | 74 | 1.6 | −10 | +9 |
| Examp. 74 | 2E | (c) | −697 | −85 | 1.7 | 722 | 76 | 1.7 | −9 | +9 |
| Examp. 75 | 2E | (d) | −698 | −86 | 1.7 | 693 | 73 | 1.6 | −11 | +7 |
| Examp. 76 | 2F | (b) | −710 | −89 | 1.8 | 711 | 69 | 1.6 | −9 | +8 |
| Examp. 77 | 2F | (c) | −723 | −87 | 1.7 | 707 | 64 | 1.5 | −10 | +10 |
| Examp. 78 | 2F | (d) | −714 | −85 | 1.7 | 699 | 65 | 1.5 | −7 | +10 |
| Examp. 79 | 2G | (b) | −693 | −91 | 1.8 | 714 | 74 | 1.7 | −8 | +8 |
| Examp. 80 | 2G | (c) | −700 | −89 | 1.8 | 705 | 78 | 1.7 | −9 | +8 |
| Examp. 81 | 2G | (d) | −714 | −88 | 1.8 | 726 | 72 | 1.6 | −8 | +9 |
| Examp. 82 | 2H | (b) | −708 | −85 | 1.7 | 711 | 75 | 1.6 | −8 | +11 |
| Examp. 83 | 2H | (c) | −703 | −87 | 1.7 | 721 | 78 | 1.7 | −11 | +10 |
| Examp. 84 | 2H | (d) | −691 | −87 | 1.7 | 708 | 71 | 1.6 | −10 | +10 |
| Comparative Examp. 15 | 2C | (a) | −705 | −118 | 2.2 | 711 | 98 | 1.9 | −28 | +23 |

As will be obvious from Table 5, the photosensitive materials for electrophotography of the present invention of Examples 67 to 84 exhibit potential after exposure, half exposure amount and repetitive property which are superior to those of the photosensitive materials of Comparative Example 15, and offer high performance from the electrophotographic point of view.

Examples 85 to 102 and Comparative Example 16

5 Parts by weight of a charge-generating material, 40 parts by weight of an electron-transporting material, 40 parts by weight of a positive hole-transporting material, 100 parts by weight of a polycarbonate resin as a binder resin, and a predetermined amount of dichloromethane as a solvent were mixed and dispersed in a ball mill to prepare a coating solution for the single layer type photosensitive material. The coating solution was applied onto an aluminum sheet using a wire bar and was dried with the hot air heated at 100° C. for 60 minutes to obtain a photosensitive material for electrophotography having a single layer type photosensitive layer which is 15 to 50 μm in thickness.

As the charge-generating material, the following compound (I) was used:

I: X-type metal-free phthalocyanine (IP=5.38 eV)

As the positive hole-transporting agent, the compounds of the following general formulas (3C) to (3H) were used:

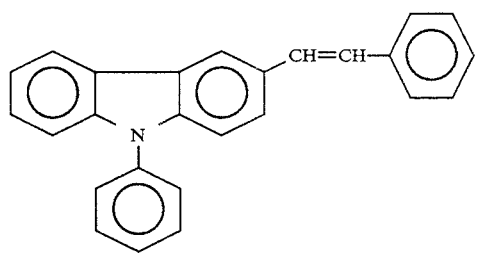

(3C)

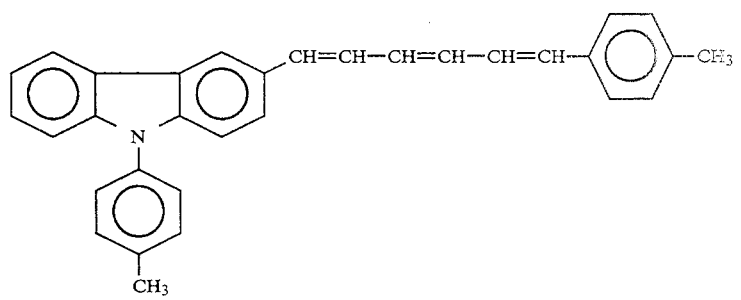

(3H)

As the electron-transporting material, the compounds of the above-mentioned formulas (a) to (d) were used as concretely shown in Table 6.

The photosensitive materials for electrophotography of the above Examples and Comparative Examples were tested for their electric properties and repetitive properties in the same manner as in Example 1 to evaluate their properties.

The results were as shown in Table 6.

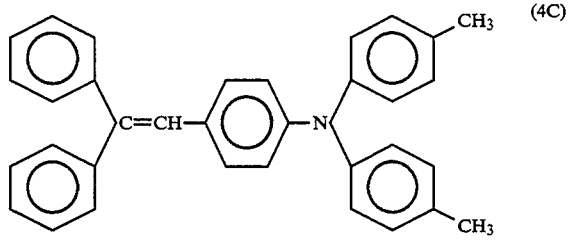
(4C)

TABLE 6

| | Hole-transporting agent | Electron-transporting agent | Photosensitivity | | | | | | Repetitive property | |
|---|---|---|---|---|---|---|---|---|---|---|
| | | | negatively charged | | | positively charged | | | | |
| | | | V1 (V) | V2 (V) | E1/2 ($\mu J/cm^2$) | V1 (V) | V2 (V) | E1/2 ($\mu J/cm^2$) | $\Delta$V1 (V) | $\Delta$V2 (V) |
| Examp. 85 | 3C | (b) | −704 | −88 | 1.7 | 722 | 79 | 1.7 | −9 | +8 |
| Examp. 86 | 3C | (c) | −715 | −89 | 1.7 | 727 | 73 | 1.6 | −10 | +6 |
| Examp. 87 | 3C | (d) | −698 | −89 | 1.7 | 694 | 74 | 1.6 | −10 | +8 |
| Examp. 88 | 3D | (b) | −717 | −87 | 1.7 | 711 | 75 | 1.6 | −9 | +8 |
| Examp. 89 | 3D | (c) | −707 | −91 | 1.9 | 703 | 68 | 1.5 | −9 | +10 |
| Examp. 90 | 3D | (d) | −699 | −87 | 1.6 | 717 | 76 | 1.6 | −6 | +10 |
| Examp. 91 | 3E | (b) | −712 | −91 | 1.8 | 713 | 72 | 1.6 | −11 | +8 |
| Examp. 92 | 3E | (c) | −716 | −67 | 1.6 | 700 | 75 | 1.7 | −11 | +6 |
| Examp. 93 | 3E | (d) | −702 | −93 | 1.8 | 703 | 81 | 1.7 | −9 | +8 |
| Examp. 94 | 3F | (b) | −710 | −88 | 1.7 | 718 | 81 | 1.7 | −12 | +9 |
| Examp. 95 | 3F | (c) | −693 | −87 | 1.6 | 699 | 67 | 1.5 | −8 | +6 |
| Examp. 96 | 3F | (d) | −705 | −89 | 1.7 | 706 | 79 | 1.7 | −9 | +7 |
| Examp. 97 | 3G | (b) | −713 | −90 | 1.8 | 717 | 71 | 1.6 | −9 | +6 |
| Examp. 98 | 3G | (c) | −723 | −93 | 1.9 | 697 | 78 | 1.7 | −9 | +8 |
| Examp. 99 | 3G | (d) | −715 | −89 | 1.7 | 726 | 78 | 1.7 | −11 | +7 |
| Examp. 100 | 3H | (b) | −700 | −88 | 1.7 | 701 | 77 | 1.7 | −8 | +9 |
| Examp. 101 | 3H | (c) | −725 | −93 | 1.9 | 716 | 72 | 1.6 | −10 | +9 |
| Examp. 102 | 3H | (d) | −695 | −95 | 1.9 | 724 | 77 | 1.7 | −9 | +10 |
| Comparative Examp. 16 | 3C | (a) | −714 | −105 | 2.0 | 705 | 96 | 1.8 | −26 | +23 |

As will be obvious from Table 6, the photosensitive materials for electrophotography of the present invention of Examples 85 to 102 exhibit potential after exposure, half exposure amount and repetitive property which are superior to those of the photosensitive materials of Comparative Example 16, and offer high performance from the electrophotographic point of view.

Examples 103 to 111 and Comparative Example 17

5 Parts by weight of a charge-generating material, 40 parts by weight of an electron-transporting material, 40 parts by weight of a positive hole-transporting material, 100 parts by weight of a polycarbonate resin as a binder resin, and a predetermined amount of dichloromethane as a solvent were mixed and dispersed in a ball mill to prepare a coating solution for the single layer type photosensitive material. The coating solution was applied onto an aluminum sheet using a wire bar and was dried with the hot air heated at 100° C. for 60 minutes to obtain a photosensitive material for electrophotography having a single layer type photosensitive layer which is 15 to 50 μm in thickness.

As the charge-generating material the following compound (I) was used:

I: X-type metal-free phthalocyanine (IP = 5.38 eV)

As the positive hole-transporting agent, the compounds of the following general formulas and (4C) to (4E) were used:

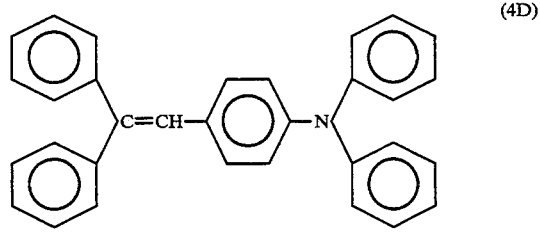
(4D)

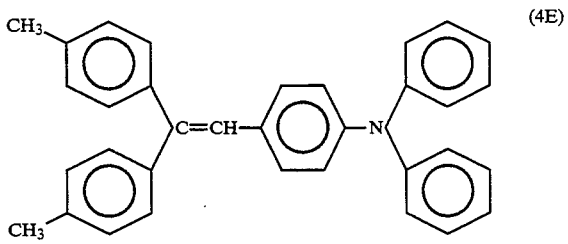
(4E)

As the electron-transporting material, the compounds of the above-mentioned formulas (a) to (d) were used as concretely shown in Table 7.

The photosensitive materials for electrophotography of the above Examples and Comparative Examples were tested for their electric properties and repetitive properties in the same manner as in Example 1 to evaluate their properties.

The results were as shown in Table 7.

TABLE 7

| | Hole-transporting agent | Electron-transporting agent | Photosensitivity | | | | | | Repetitive property | |
|---|---|---|---|---|---|---|---|---|---|---|
| | | | negatively charged | | | positively charged | | | | |
| | | | V1 (V) | V2 (V) | E1/2 (μJ/cm²) | V1 (V) | V2 (V) | E1/2 (μJ/cm²) | ΔV1 (V) | ΔV2 (V) |
| Examp. 103 | 4C | (b) | −711 | −85 | 1.7 | 711 | 70 | 1.8 | −9 | +12 |
| Examp. 104 | 4C | (c) | −713 | −86 | 1.7 | 712 | 78 | 1.7 | −8 | +10 |
| Examp. 105 | 4C | (d) | −708 | −91 | 1.8 | 720 | 76 | 1.7 | −8 | +7 |
| Examp. 106 | 4D | (b) | −713 | −90 | 1.8 | 713 | 71 | 1.6 | −9 | +9 |
| Examp. 107 | 4D | (c) | −695 | −94 | 1.9 | 699 | 78 | 1.7 | −7 | +12 |
| Examp. 108 | 4D | (d) | −703 | −86 | 1.7 | 722 | 75 | 1.6 | −10 | +10 |
| Examp. 109 | 4E | (b) | −699 | −90 | 1.8 | 693 | 64 | 1.5 | −12 | +8 |
| Examp. 110 | 4E | (c) | −709 | −86 | 1.7 | 715 | 64 | 1.5 | −10 | +12 |
| Examp. 111 | 4E | (d) | −720 | −89 | 1.8 | 702 | 70 | 1.6 | −7 | +9 |
| Comparative Examp. 17 | 4C | (a) | −723 | −111 | 2.0 | 706 | 96 | 2.0 | −35 | +28 |

As will be obvious from Table 7, the photosensitive materials for electrophotography of the present invention of Examples 103 to 111 exhibit potential after exposure, half exposure amount and repetitive property which are superior to those of the photosensitive materials of Comparative Example 17, and offer high performance from the electrophotographic point of view.

Examples 112 to 138 and Comparative Example 18

5 Parts by weight of a charge-generating material, 40 parts by weight of an electron-transporting material, 40 parts by weight of a positive hole-transporting material, 100 parts by weight of a polycarbonate resin as a binder resin, and a predetermined amount of dichloromethane as a solvent were mixed and dispersed in a ball mill to prepare a coating solution for the single layer type photosensitive material. The coating solution was applied onto an aluminum sheet using a wire bar and was dried with the hot air heated at 100° C. for 60 minutes to obtain a photosensitive material for electrophotography having a single layer type photosensitive layer which is 15 to 50 μm in thickness.

As the charge-generating material, the following compound (I) was used:

I: X-type metal-free phthalocyanine (IP=5.38 eV)

As the positive hole-transporting agent, the compounds of the following general formulas (5C) to (5K) were used:

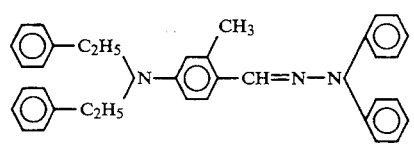
(5C)

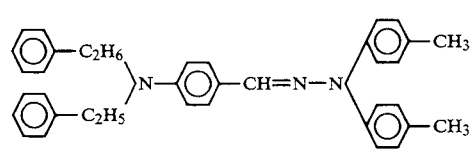
(5D)

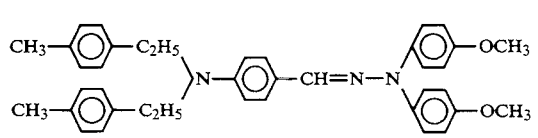
(5E)

-continued

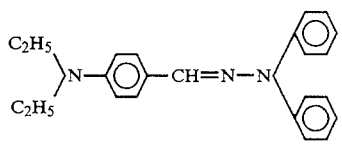
(5F)

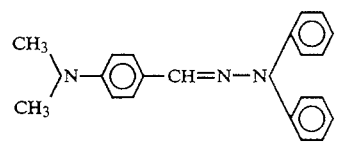
(5G)

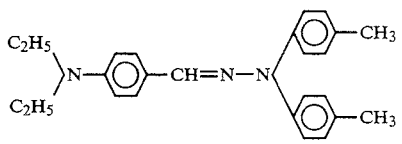
(5H)

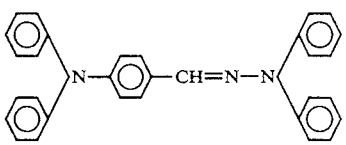
(5I)

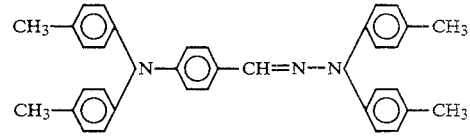
(5J)

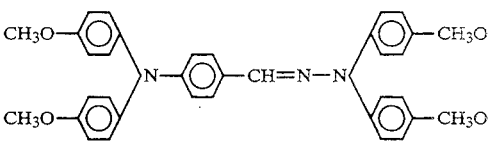
(5K)

As the electron-transporting material, the compounds of the above-mentioned formulas (a) to (d) were used as concretely shown in Table 8.

The photosensitive materials for electrophotography of the above Examples and Comparative Examples were tested for their electric properties and repetitive properties in the same manner as in Example 1 to evaluate their properties.

The results were as shown in Tables 8, 9 and 10.

TABLE 8

| | Hole-transporting agent | Electron-transporting agent | Photosensitivity negatively charged V1 (V) | V2 (V) | E1/2 ($\mu J/cm^2$) | positively charged V1 (V) | V2 (V) | E1/2 ($\mu J/cm^2$) | Repetitive property $\Delta$V1 (V) | $\Delta$V2 (V) |
|---|---|---|---|---|---|---|---|---|---|---|
| Examp. 112 | 5C | (b) | −706 | −86 | 1.8 | 704 | 66 | 1.5 | −11 | +7 |
| Examp. 113 | 5C | (c) | −703 | −82 | 1.7 | 706 | 74 | 1.7 | −9 | +6 |
| Examp. 114 | 5C | (d) | −704 | −81 | 1.7 | 703 | 73 | 1.7 | −7 | +8 |
| Examp. 115 | 5D | (b) | −701 | −89 | 1.8 | 700 | 77 | 1.8 | −7 | +9 |
| Examp. 116 | 5D | (c) | −705 | −91 | 1.9 | 704 | 78 | 1.8 | −6 | +10 |
| Examp. 117 | 5D | (d) | −700 | −86 | 1.8 | 706 | 74 | 1.7 | −8 | +8 |
| Examp. 118 | 5E | (b) | −702 | −84 | 1.7 | 709 | 76 | 1.7 | −9 | +7 |
| Examp. 119 | 5E | (c) | −700 | −83 | 1.7 | 700 | 75 | 1.7 | −7 | +10 |
| Examp. 120 | 5E | (d) | −699 | −87 | 1.7 | 701 | 73 | 1.7 | −10 | +8 |
| Comparative Examp. 18 | 5C | (a) | −700 | −125 | 2.3 | 699 | 96 | 1.9 | −25 | +23 |

TABLE 9

| | Hole-transporting agent | Electron-transporting agent | Photosensitivity negatively charged V1 (V) | V2 (V) | E1/2 ($\mu J/cm^2$) | positively charged V1 (V) | V2 (V) | E1/2 ($\mu J/cm^2$) | Repetitive property $\Delta$V1 (V) | $\Delta$V2 (V) |
|---|---|---|---|---|---|---|---|---|---|---|
| Examp. 121 | 5F | (b) | −700 | −90 | 1.9 | 709 | 74 | 1.7 | −5 | +8 |
| Examp. 122 | 5F | (c) | −892 | −84 | 1.8 | 705 | 68 | 1.6 | −3 | +10 |
| Examp. 123 | 5F | (d) | −698 | −88 | 1.9 | 700 | 71 | 1.6 | −8 | +6 |
| Examp. 124 | 5G | (b) | −708 | −81 | 1.7 | 697 | 79 | 1.7 | −10 | +5 |
| Examp. 125 | 5G | (c) | −706 | −85 | 1.8 | 704 | 75 | 1.6 | −7 | +8 |
| Examp. 126 | 5G | (d) | −707 | −85 | 1.8 | 707 | 70 | 1.6 | −8 | +11 |
| Examp. 127 | 5H | (b) | −701 | −87 | 1.8 | 696 | 75 | 1.7 | −12 | +8 |
| Examp. 128 | 5H | (c) | −700 | −82 | 1.7 | 705 | 69 | 1.6 | −7 | +6 |
| Examp. 129 | 5H | (d) | −708 | −86 | 1.8 | 697 | 77 | 1.7 | −9 | +9 |

TABLE 10

| | Hole-transporting agent | Electron-transporting agent | Photosensitivity negatively charged V1 (V) | V2 (V) | E1/2 ($\mu J/cm^2$) | positively charged V1 (V) | V2 (V) | E1/2 ($\mu J/cm^2$) | Repetitive property $\Delta$V1 (V) | $\Delta$V2 (V) |
|---|---|---|---|---|---|---|---|---|---|---|
| Examp. 130 | 5I | (b) | −692 | −88 | 1.7 | 709 | 79 | 1.7 | −12 | +11 |
| Examp. 131 | 5I | (c) | −709 | −89 | 1.7 | 712 | 73 | 1.6 | −11 | +12 |
| Examp. 132 | 5I | (d) | −701 | −92 | 1.8 | 706 | 75 | 1.7 | −9 | +9 |
| Examp. 133 | 5J | (b) | −715 | −88 | 1.7 | 700 | 65 | 1.6 | −10 | +11 |
| Examp. 134 | 5J | (c) | −711 | −87 | 1.7 | 712 | 74 | 1.6 | −9 | +9 |
| Examp. 135 | 5J | (d) | −698 | −92 | 1.8 | 723 | 75 | 1.7 | −11 | +10 |
| Examp. 136 | 5K | (b) | −706 | −94 | 1.9 | 717 | 69 | 1.6 | −9 | +9 |
| Examp. 137 | 5K | (c) | −716 | −92 | 1.8 | 716 | 73 | 1.6 | −10 | +11 |
| Examp. 138 | 5K | (d) | −697 | −89 | 1.7 | 699 | 74 | 1.6 | −11 | +12 |

As will be obvious from Tables 8, 9 and 10, the photosensitive materials for electrophotography of the present invention of Examples 112 to 138 exhibit potential after exposure, half exposure amount and repetitive property which are superior to those of the photosensitive materials of Comparative Example 18, and offer high performance from the electrophotographic point of view.

Examples 139 to 147 and Comparative Example 19

5 Parts by weight of a charge-generating material, 40 parts by weight of an electron-transporting material, 40 parts by weight of a positive hole-transporting material, 100 parts by weight of a polycarbonate resin as a binder resin, and a predetermined amount of dichloromethane as a solvent were mixed and dispersed in a ball mill to prepare a coating solution for the single layer type photosensitive material. The coating solution was applied onto an aluminum sheet using a wire bar and was dried with the hot air heated at 100° C. for 60 minutes no obtain a photosensitive material for electrophotography having a single layer type photosensitive layer which is 15 to 50 pm in thickness.

As the charge-generating material, the following compounds (I) and (II) were used:

I: X-type metal-free phthalocyanine (IP=5.38 eV)

As the positive hole-transporting agent, the compounds of the following general formulas (6C) to (6E) were used:

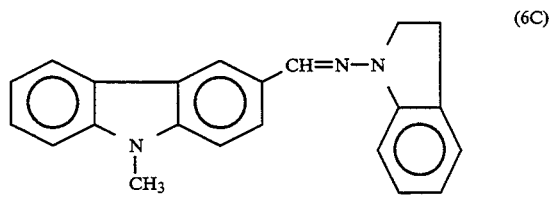

(6C)

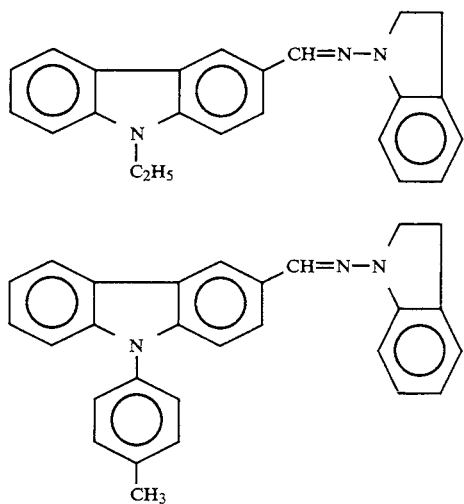

(6D)

(6E)

As the electron-transporting material, the compounds of the above-mentioned formulas (a) to (d) were used as concretely shown in Table 11.

The photosensitive materials for electrophotography of the above Examples and Comparative Examples were tested for their electric properties and repetitive properties in the same manner as in Example 1 to evaluate their properties.

The results were as shown in Table 11.

resin, and a predetermined amount of dichloromethane as a solvent were mixed and dispersed in a ball mill to prepare a coating solution for the single layer type photosensitive material. The coating solution was applied onto an aluminum sheet using a wire bar and was dried with the hot air heated at 100° C. for 60 minutes to obtain a photosensitive material for electrophotography having a single layer type photosensitive layer which is 15 to 50 μm in thickness.

As the charge-generating material, the following compound (I) was used:

I: X-type metal-free phthalocyanine (IP=5.38 eV)

As the positive hole-transporting agent, the compounds of the following general formulas (7C) to (7E) were used:

(7C)

(7D)

(7E)

TABLE 11

| | Hole-transporting agent | Electron-transporting agent | Photosensitivity | | | | | | Repetitive property | |
|---|---|---|---|---|---|---|---|---|---|---|
| | | | negatively charged | | | positively charged | | | | |
| | | | V1 (V) | V2 (V) | E1/2 (μJ/cm²) | V1 (V) | V2 (V) | E1/2 (μJ/cm²) | ΔV1 (V) | ΔV2 (V) |
| Examp. 139 | 6C | (b) | −709 | −82 | 1.7 | 704 | 74 | 1.7 | −10 | +10 |
| Examp. 140 | 6C | (c) | −711 | −86 | 1.8 | 706 | 73 | 1.6 | −8 | +9 |
| Examp. 141 | 6C | (d) | −690 | −88 | 1.8 | 700 | 73 | 1.6 | −10 | +10 |
| Examp. 142 | 6D | (b) | −699 | −83 | 1.7 | 704 | 70 | 1.5 | −10 | +7 |
| Examp. 143 | 6D | (c) | −702 | −80 | 1.7 | 701 | 68 | 1.5 | −11 | +7 |
| Examp. 144 | 6D | (d) | −706 | −87 | 1.8 | 700 | 74 | 1.7 | −9 | +6 |
| Examp. 145 | 6E | (b) | −698 | −88 | 1.8 | 696 | 79 | 1.6 | −7 | +10 |
| Examp. 146 | 6E | (c) | −705 | −86 | 1.8 | 699 | 74 | 1.7 | −6 | +7 |
| Examp. 147 | 6E | (d) | −707 | −90 | 1.9 | 700 | 72 | 1.6 | −8 | +11 |
| Comparative Examp. 19 | 6C | (a) | −699 | −111 | 2.2 | 704 | 96 | 2.0 | −25 | +22 |

As will be obvious from Table 11, the photosensitive materials for electrophotography of the present invention of Examples 139 to 147 exhibit potential after exposure, half exposure amount and repetitive property which are superior to those of the photosensitive materials of Comparative Example 19, and offer high performance from the electrophotographic point of view.

Examples 148 to 156 and Comparative Example 20

5 Parts by weight of a charge-generating material, 40 parts by weight of an electron-transporting material, 40 parts by weight of a positive hole-transporting material, 100 parts by weight of a polycarbonate resin as a binder resin, and a predetermined amount of dichloromethane as a solvent were mixed and dispersed in a ball mill to prepare a coating solution for the single layer type photosensitive material. The coating solution was applied onto an aluminum sheet using a wire bar and was dried with the hot air heated at 100° C. for 60 minutes to obtain a photosensitive material for electrophotography having a single layer type photosensitive layer which is 15 to 50 μm in thickness.

As the electron-transporting material, the compounds of the above-mentioned formulas (a) to (d) were used as concretely shown in Table 12.

The photosensitive materials for electrophotography of the above Examples and Comparative Examples were tested for their electric properties and repetitive properties in the same manner as in Example 1 to evaluate their properties.

TABLE 12

| | Hole-transporting agent | Electron-transporting agent | Photosensitivity | | | | | | Repetitive property | |
|---|---|---|---|---|---|---|---|---|---|---|
| | | | negatively charged | | | positively charged | | | | |
| | | | V1 (V) | V2 (V) | E1/2 (μJ/cm²) | V1 (V) | V2 (V) | E1/2 (μJ/cm²) | ΔV1 (V) | ΔV2 (V) |
| Examp. 148 | 7C | (b) | −701 | −82 | 1.7 | 704 | 74 | 1.7 | −10 | +8 |

TABLE 12-continued

| | Hole-transporting agent | Electron-transporting agent | Photosensitivity | | | | | | Repetitive property | |
|---|---|---|---|---|---|---|---|---|---|---|
| | | | negatively charged | | | positively charged | | | | |
| | | | V1 (V) | V2 (V) | E1/2 ($\mu J/cm^2$) | V1 (V) | V2 (V) | E1/2 ($\mu J/cm^2$) | ΔV1 (V) | ΔV2 (V) |
| Examp. 149 | 7C | (c) | −698 | −86 | 1.8 | 702 | 70 | 1.6 | −11 | +9 |
| Examp. 150 | 7C | (d) | −707 | −87 | 1.8 | 700 | 76 | 1.7 | −8 | +10 |
| Examp. 151 | 7D | (b) | −691 | −90 | 1.9 | 703 | 72 | 1.6 | −6 | +10 |
| Examp. 152 | 7D | (c) | −704 | −84 | 1.8 | 701 | 69 | 1.6 | −9 | +8 |
| Examp. 153 | 7D | (d) | −706 | −83 | 1.8 | 699 | 76 | 1.6 | −7 | +10 |
| Examp. 154 | 7E | (b) | −699 | −68 | 1.9 | 703 | 74 | 1.7 | −10 | +7 |
| Examp. 155 | 7E | (c) | −700 | −86 | 1.8 | 708 | 72 | 1.7 | −8 | +8 |
| Examp. 156 | 7E | (d) | −702 | −88 | 1.8 | 710 | 68 | 1.6 | −7 | +6 |
| Comparative Examp. 20 | 7C | (a) | −698 | −120 | 2.2 | 710 | 94 | 2.0 | −26 | +21 |

As will be obvious from Table 12, the photosensitive materials for electrophotography of the present invention of Examples 148 to 156 exhibit potential after exposure, half exposure amount and repetitive property which are superior to those of the photosensitive materials of Comparative Example 20, and offer high performance from the electrophotographic point of view.

Examples 157 to 165 and Comparative Example 21

5 Parts by weight of a charge-generating material, 40 parts by weight of an electron-transporting material 40 parts by weight of a positive hole-transporting material, 100 parts by weight of a polycarbonate resin as a binder resin, and a predetermined amount of dichloromethane as a solvent were mixed and dispersed in a ball mill to prepare a coating solution for the single layer type photosensitive material. The coating solution was applied onto an aluminum sheet using a wire bar and was dried with the hot air heated at 100° C. for 60 minutes to obtain a photosensitive material for electrophotography having a single layer type photosensitive layer which is 15 to 50 μm in thickness.

As the charge-generating material, the following compound (I) was used:

I: X-type metal-free phthalocyanine (IP=5.38 eV)

As the positive hole-transporting agent, the compounds of the following general formulas (8C) to (8E) were used:

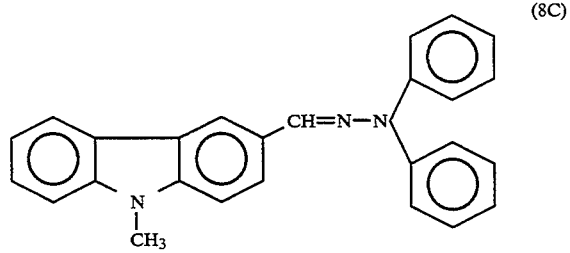

(8C)

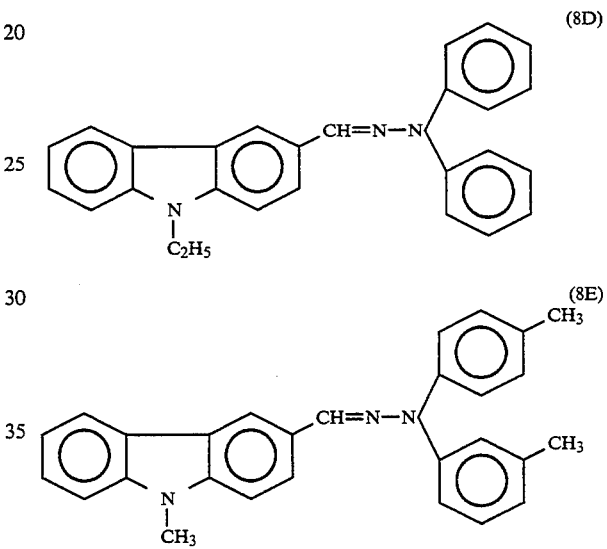

(8D)

(8E)

As the electron-transporting material, the compounds of the above-mentioned formulas (a) to (d) were used as concretely shown in Table 13.

The photosensitive materials for electrophotography of the above Examples and Comparative Examples were tested for their electric properties and repetitive properties in the same manner as in Example 1 to evaluate their properties. The results were as shown in Table 13.

TABLE 13

| | Hole-transporting agent | Electron-transporting agent | Photosensitivity | | | | | | Repetitive property | |
|---|---|---|---|---|---|---|---|---|---|---|
| | | | negatively charged | | | positively charged | | | | |
| | | | V1 (V) | V2 (V) | E1/2 ($\mu J/cm^2$) | V1 (V) | V2 (V) | E1/2 ($\mu J/cm^2$) | ΔV1 (V) | ΔV2 (V) |
| Examp. 157 | 8C | (b) | −694 | −85 | 1.8 | 701 | 75 | 1.7 | −8 | +10 |
| Examp. 158 | 8C | (c) | −700 | −90 | 1.9 | 704 | 71 | 1.6 | −10 | +9 |
| Examp. 159 | 8C | (d) | −705 | −91 | 1.9 | 698 | 74 | 1.7 | −6 | +11 |
| Examp. 160 | 8D | (b) | −692 | −87 | 1.8 | 697 | 70 | 1.6 | −7 | +8 |
| Examp. 161 | 8D | (c) | −710 | −86 | 1.8 | 701 | 69 | 1.6 | −8 | +7 |
| Examp. 162 | 8D | (d) | −709 | −88 | 1.9 | 703 | 72 | 1.7 | −11 | +8 |
| Examp. 163 | 8E | (b) | −707 | −81 | 1.7 | 700 | 68 | 1.6 | −7 | +10 |

TABLE 13-continued

|  | Hole-transporting agent | Electron-transporting agent | Photosensitivity | | | | | | Repetitive property | |
|---|---|---|---|---|---|---|---|---|---|---|
|  |  |  | negatively charged | | | positively charged | | | | |
|  |  |  | V1 (V) | V2 (V) | E1/2 (μJ/cm²) | V1 (V) | V2 (V) | E1/2 (μJ/cm²) | ΔV1 (V) | ΔV2 (V) |
| Examp. 164 | 8E | (c) | −701 | −84 | 1.8 | 706 | 74 | 1.7 | −9 | +7 |
| Examp. 165 | 8E | (d) | −708 | −85 | 1.8 | 704 | 76 | 1.7 | −5 | +10 |
| Comparative Examp. 21 | 8C | (a) | −704 | −114 | 2.1 | 709 | 97 | 2.0 | −27 | +20 |

As will be obvious from Table 13, the photosensitive materials for electrophotography of the present invention of Examples 157 to 165 exhibit potential after exposure, half exposure amount and repetitive property which are superior to those of the photosensitive materials of Comparative Example 21, and offer high performance from the electrophotographic point of view.

Examples 166 to 174 and Comparative Example 22

5 Parts by weight of a charge-generating material, 40 parts by weight of an electron-transporting material, 40 parts by weight of a positive hole-transporting material, 100 parts by weight of a polycarbonate resin as a binder resin, and a predetermined amount of dichloromethane as a solvent were mixed and dispersed in a ball mill to prepare a coating solution for the single layer type photosensitive material. The coating solution was applied onto an aluminum sheet using a wire bar and was dried with the hot air heated at 100° C. for 60 minutes to obtain a photosensitive material for electrophotography having a single layer type photosensitive layer which is 15 to 50 μm in thickness.

As the charge-generating material, the following compound (I) was used:

I: X-type metal-free phthalocyanine (IP=5.38 eV)

As the positive hole-transporting agent, the compounds of the following general formulas (9C) to (9E) were used:

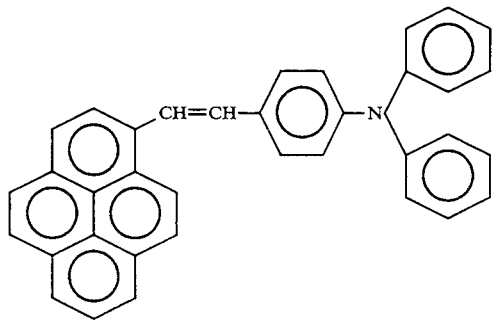

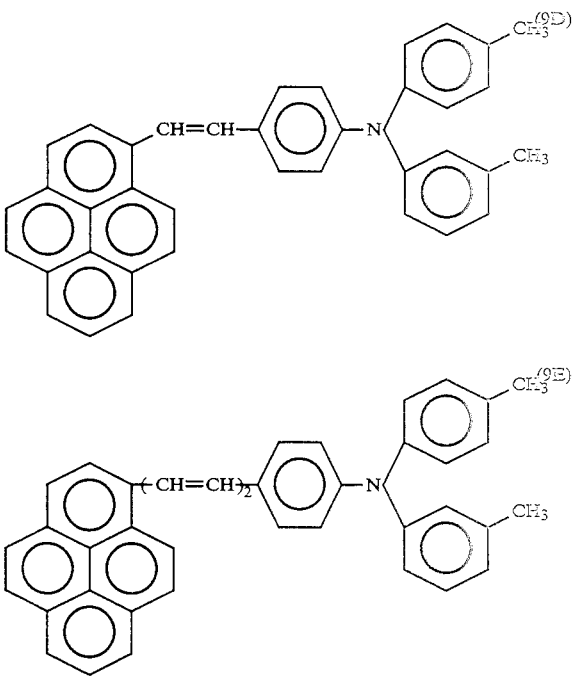

As the electron-transporting material, the compounds of the above-mentioned formulas (a) to (d) were used as concretely shown in Table 14.

The photosensitive materials for electrophotography of the above Examples and Comparative Examples were tested for their electric properties and repetitive properties in the same manner as in Example 1 to evaluate their properties. The results were as shown in Table 14.

TABLE 14

|  | Hole-transporting agent | Electron-transporting agent | Photosensitivity | | | | | | Repetitive property | |
|---|---|---|---|---|---|---|---|---|---|---|
|  |  |  | negatively charged | | | positively charged | | | | |
|  |  |  | V1 (V) | V2 (V) | E1/2 (μJ/cm²) | V1 (V) | V2 (V) | E1/2 (μJ/cm²) | ΔV1 (V) | ΔV2 (V) |
| Examp. 166 | 9C | (b) | −705 | −86 | 1.8 | 698 | 71 | 1.6 | −7 | +8 |
| Examp. 167 | 9C | (c) | −700 | −88 | 1.9 | 697 | 68 | 1.5 | −9 | +9 |
| Examp. 168 | 9C | (d) | −699 | −87 | 1.8 | 705 | 72 | 1.7 | −10 | +6 |
| Examp. 169 | 9D | (b) | −698 | −90 | 1.9 | 706 | 75 | 1.8 | −8 | +11 |
| Examp. 170 | 9D | (c) | −704 | −85 | 1.8 | 702 | 74 | 1.8 | −7 | +7 |
| Examp. 171 | 9D | (d) | −696 | −86 | 1.8 | 700 | 70 | 1.7 | −11 | +10 |
| Examp. 172 | 9E | (b) | −705 | −89 | 1.9 | 702 | 78 | 1.8 | −10 | +10 |
| Examp. 173 | 9E | (c) | −709 | −90 | 1.9 | 701 | 66 | 1.5 | −9 | +9 |
| Examp. 174 | 9E | (d) | −704 | −85 | 1.8 | 699 | 74 | 1.8 | −8 | +8 |
| Comparative Examp. 22 | 9C | (a) | −706 | −116 | 2.1 | 711 | 97 | 2.0 | −25 | +19 |

As will be obvious from Table 14, the photosensitive materials for electrophotography of the present invention of Examples 166 to 174 exhibit potential after exposure, half exposure amount and repetitive property which are superior to those of the photosensitive materials of Comparative Example 22, and offer high performance from the electrophotographic point of view.

We claim:

1. A photosensitive material for electrophotography comprising an organic photosensitive layer containing
   1 to 20 parts by weight of a charge-generating agent, 10 to 100 parts by weight of a diphenoquinone electron-transporting agent, 10 to 100 parts by weight of a positive hole-transporting agent and 100 parts by weight of a binder,
   wherein the diphenoquinone is represented by the following formula (1):

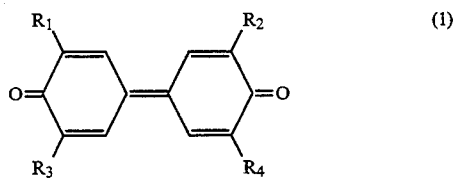

(1)

wherein at least three $R_1$ to $R_4$ groups are different from each other and $R_1$ is a tertiary alkyl group having 4 to 9 carbon atoms, $R_3$ is a phenyl group or a benzyl group and $R_2$ and $R_4$ are primary or secondary alkyl groups or alkoxy groups having 1 to 4 carbons atoms, and
   wherein the diphenoquinone is in an amount of 20 to 80% by weight based on the amount of the diphenoquinone and the positive hole-transporting agent.

2. An organic photosensitive material according to claim 1, wherein the diphenoquinone derivative is a 3,5-diisopropyl-3′-butyl-5′-phenyl-4,4′-diphenoquinone.

3. An organic photosensitive material according to claim 1, wherein the diphenoquinone derivative is a 3,5-diisopropyl-3′-(α,α,γ,γ-tetramethylbutyl)-5′-phenyl-4,4′-diphenoquinone.

4. An organic photosensitive material according to claim 1, wherein the diphenoquinone derivative is a 3,5-di-sec-butyl-3′-t-butyl-5′-phenyl-4,4′-diphenoquinone.

5. An organic photosensitive material according to claim 1, wherein the diphenoquinone derivative is a 3,5-dimethyl-3′-sec-butyl-5′-cumyl-4,4′-diphenoquinone.

6. A photosensitive material for electrophotography comprising an electrically conducting substrate on which is provided a photosensitive layer containing
   1 to 20 parts by weight of a charge-generating agent, a charge transporting material consisting essentially of 10 to 100 parts by weight of a diphenoquinone electron-transporting agent and 10 to 100 parts by weight of a positive hole-transporting agent, and 100 parts by weight of a binder, and
   wherein the diphenoquinone is represented by the following formula (1):

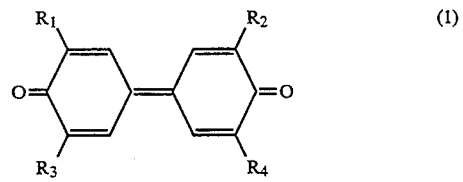

(1)

wherein at least three $R_1$ to $R_4$ groups are different from each other and $R_1$ is a tertiary alkyl group having 4 to 9 carbon atoms, $R_3$ is a phenyl group or a benzyl group and $R_2$ and $R_4$ are primary or secondary alkyl groups or alkoxy groups having 1 to 4 carbon atoms,
   wherein the diphenoquinone is in an amount of 20 to 80% by weight based on the amount of the diphenoquinone and the positive hole-transporting agent, and
   wherein the positive hole-transporting agent is at least one member selected from the formula (2) to (11).

7. A photosensitive material according to claim 6, wherein the positive hole-transporting agent is a compound represented by the following general formula (2);

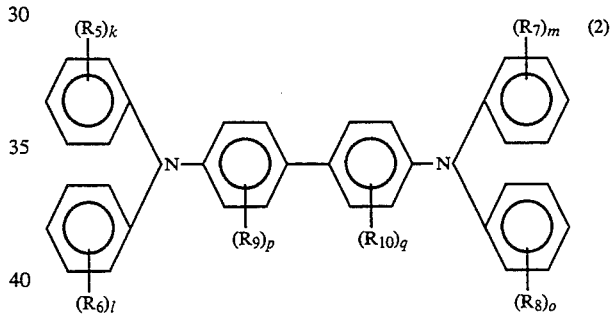

(2)

wherein $R_5$, $R_6$, $R_7$, $R_8$, $R_9$ and $R_{10}$ are alkyl groups, alkoxy groups, halogen atoms, aryl groups, nitro groups, cyano groups or alkylamino groups independently of each other, p and q are integers of 0 to 4, and k, l, m and o are integers of 0 to 5.

8. A photosensitive material according to claim 6, wherein the positive hole-transporting agent is a compound represented by the following general formula (3);

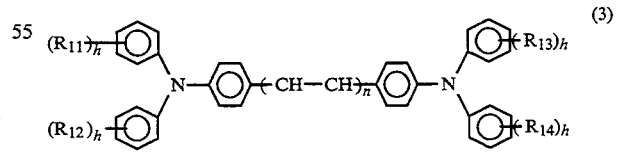

(3)

wherein $R_{11}$, $R_{12}$, $R_{13}$ and $R_{14}$ are hydrogen atoms, alkyl groups or alkoxy groups, and n and h are integers of 1 to 3.

9. A photosensitive material according to claim 6, wherein the positive hole-transporting agent is a compound represented by the following general formula (4);

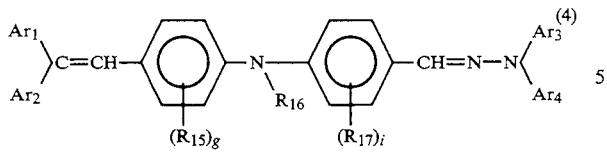

(4)

wherein $R_{15}$ and $R_{17}$ are alkyl groups, alkoxy groups or halogen atoms, g and i are integers of 0 to 4, $R_{16}$ is a hydrogen atom, an alkyl group which may have a substituent, an aralkyl group, an aryl group, or a heterocyclic group, $Ar_1$ and $Ar_2$ are alkyl groups, aralkyl groups, aryl groups or heterocyclic groups which may have substituents but $Ar_1$ and $Ar_2$ may be coupled together to form a ring except when $Ar_1$ and $Ar_2$ are hydrogen atoms simultaneously and $Ar_3$ and $Ar_4$ are alkyl groups, aralkyl groups, aryl groups or heterocyclic rings which may have substituents but $Ar_3$ and $Ar_4$ may be coupled together to form a ring.

10. A photosensitive material according to claim 6, wherein the positive hole-transporting agent is a compound represented by the following general formula (5);

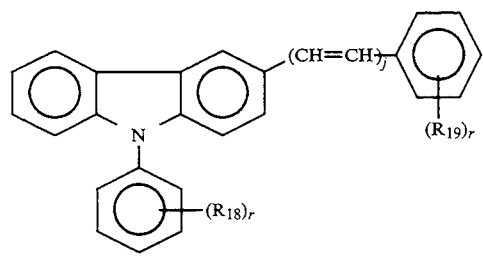

(5)

wherein $R_{18}$ and $R_{19}$ are alkyl groups or alkoxy groups, and j and r are integers of 0 to 3.

11. A photosensitive material according to claim 6, wherein the positive hole-transporting agent is a compound represented by the following general formula (6);

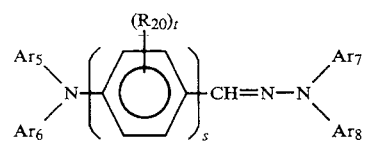

(6)

wherein $R_{20}$ is an alkyl group or an alkoxy group, $Ar_5$, $Ar_6$, $Ar_7$ and $Ar_8$ are hydrogen atoms, alkyl groups, alkoxy groups, aralkyl groups or aryl groups which may have a substituent, and s is an integer of 1 to 2, and t is an integer of 0 to 2.

12. A photosensitive material according to claim 6, wherein the positive hole-transporting agent is a compound represented by the following general formula (7);

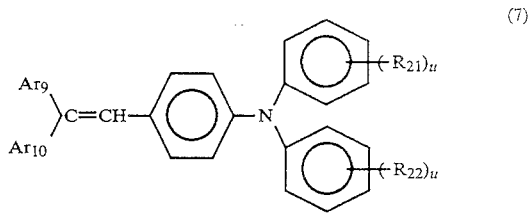

(7)

wherein $R_{21}$ and $R_{22}$ are alkyl groups or alkoxy groups, u is an integer of 0 to 2, and $Ar_9$ and $Ar_{10}$ are aryl groups which may have a substituent.

13. A photosensitive material according to claim 6, wherein the positive hole-transporting agent is a compound represented by the following general formula (8);

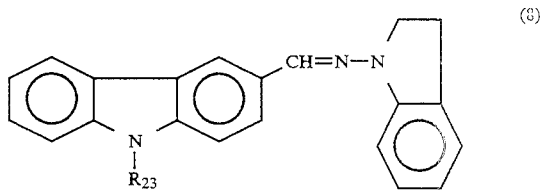

(8)

wherein $R_{23}$ is an alkyl group or an aryl group.

14. A photosensitive material according to claim 6, wherein the positive hole-transporting agent is a compound represented by the following general formula (9);

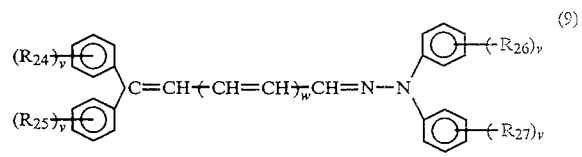

(9)

wherein $R_{24}$, $R_{25}$, $R_{26}$ and $R_{27}$ are alkyl groups or alkoxy groups, and v and w are integers of 0 to 3.

15. A photosensitive material according to claim 6, wherein the positive hole-transporting agent is a compound represented by the following general formula (10);

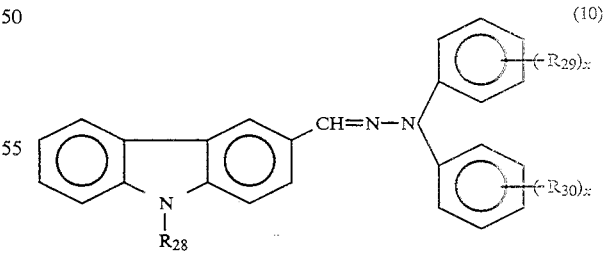

(10)

wherein $R_{28}$ is a alkyl group or an aryl group, $R_{29}$ and $R_{30}$ are alkyl groups or alkoxy groups independently from each other, and x is an integer of 0 to 3.

16. A photosensitive material according to claim 6, wherein the positive hole-transporting agent is a compound represented by the following general formula (11);

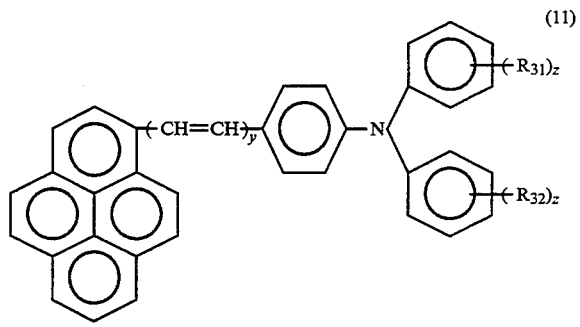

(11)

wherein $R_{31}$ and $R_{32}$ are alkyl groups or alkoxy groups, and y and z are integers of 0 to 3.

17. An organic photosensitive material according to claim 6, wherein the diphenoquinone derivative is a 3,5-diisopropyl-3'-t-butyl-5'-phenyl-4,4'-diphenoquinone.

18. An organic photosensitive material according to claim 6, wherein the diphenoquinone derivative is a 3,5-diisopropyl-3'-α,α,γ,γ-tetramethylbutyl)-5'-phenyl-4,4'-diphenoquinone.

19. An organic photosensitive material according to claim 6, wherein the diphenoquinone derivative is a 3,5-di-sec-butyl-3'-t-butyl-5'-phenyl-4,4'-diphenoquinone.

20. An organic photosensitive material according to claim 6, wherein the diphenoquinone derivative is a 3,5-dimethyoxy-3'-(α,α, γ,γ-tetramethylbutyl)-5'-phenyl-4,4'-diphenoquinone.

21. An organic photosensitive material according to claim 6, wherein the diphenoquinone derivative is a 3,5-dimethyl-3'-sec-butyl-5'-cumyl-4,4'-diphenoquinone.

22. An organic photosensitive material for electrophotography comprising an organic photosensitive layer containing
1 to 20 parts by weight of a charge-generating agent, 10 to 100 parts by weight of a diphenoquinone electron-transporting agent, 10 to 100 parts by weight of a positive hole-transporting agent and 100 parts by weight of a binder,
wherein the diphenoquinone is a 3,5-dimethyoxy-3'-(α,α,γ,γ-tetramethylbutyl)-5'-phenyl-4,4'-diphenoquinone, and
wherein the diphenoquinone is in an amount of 20 to 80% by weight based on the amount of the diphenoquinone and the positive hole-transporting agent.

23. A laminated photosensitive material for electrophotography comprising a charge generating layer containing 50 to 500 parts by weight of a charge generating agent and 100 parts by weight of a binder, and
an electron transporting layer containing 10 to 100 parts by weight of a diphenoquinone electron-transporting agent 10 to 100 parts by weight of a positive hole transporting agent, and 100 parts by weight of a binder,
wherein the diphenoquinone is represented by the following formula (1)

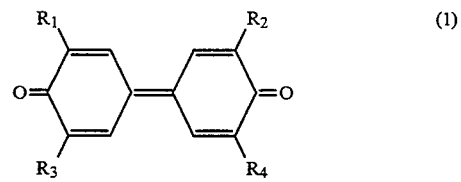

(1)

wherein $R_1$, $R_2$, $R_3$ and $R_4$ are alkyl groups, alkoxy groups, aryl groups or aralkyl groups, and at least one of $R_1$, $R_2$, $R_3$ and $R_4$ is an aryl group or an aralkyl group, and at least 2 of the remaining $R_1$, $R_2$, $R_3$ and $R_4$ are alkyl groups or alkoxy groups, and
wherein the diphenoquinone is in an amount of 20 to 80% by weight based on the amount of the diphenoquinone and the positive hole-transporting agent.

24. An organic photosensitive material according to claim 23, wherein at least one of $R_1$, $R_2$, $R_3$ and $R_4$ in said general formula (1) is a branched chain alkyl group with 3 to 9 carbon atoms.

25. An organic photosensitive material according to claim 23, wherein $R_1$ is a tertiary alkyl group with 4 to 9 carbon atoms, $R_3$ is a phenyl group or a benzyl group, and $R_2$ and $R_4$ are primary or secondary alkyl groups or alkoxy groups.

26. An organic photosensitive material according to claim 23, wherein the diphenoquinone derivative is a 3,5-diisopropyl-3'-t-butyl-5'-phenyl-4,4'-diphenoquinone.

27. An organic photosensitive material according to claim 23, wherein the diphenoquinone derivative is a 3,5-diisopropyl-3'-(α,α,γ,γ-tetramethylbutyl)-5'-phenyl-4,4'-diphenoquinone.

28. An organic photosensitive material according to claim 23, wherein the diphenoquinone derivative is a 3,5-di-sec-butyl-3'-t-butyl-5-phenyl-4,4'-diphenoquinone.

29. An organic photosensitive material according to claim 23, wherein the diphenoquinone derivative is a 3,5-dimethoxy-3'-(α,α,γ,γ-tetramethylbutyl)-5'-phenyl-4,4'-diphenoquinone.

30. An organic photosensitive material according to claim 23, wherein the diphenoquinone derivative is a 3,5-dimethyl-3'-sec-butyl-5'-cumyl-4,4'-diphenoquinone.

31. A photosensitive material for electrophotography comprising an electrically conductive substrate on which is provided a laminated photosensitive layer comprising
a charge generating layer containing 50 to 500 parts by weight of a charge generating agent and 100 parts by weight of a binder, and
an electron transporting layer containing 10 to 100 parts by weight of a diphenoquinone electron-transporting agent, 10 to 100 parts by weight of a positive hole transporting agent, and 100 parts by weight of a binder,
wherein the diphenoquinone is represented by the following formula (1)

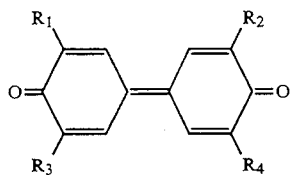

(1)

wherein $R_1$, $R_2$, $R_3$ and $R_4$ are alkyl groups, alkoxy groups, aryl groups or aralkyl groups, and at least one of $R_1$, $R_2$, $R_3$ and $R_4$ is an aryl group or an aralkyl group, and at least 2 of the remaining $R_1$, $R_2$, $R_3$ and $R_4$ are alkyl groups or alkoxy groups, wherein the diphenoquinone is in an amount of 20 to 80% by weight based on the amount of the diphenoquinone and the positive hole-transporting agent, and wherein the positive hole-transporting agent is at least one member selected from the below formulas (2) to (11),

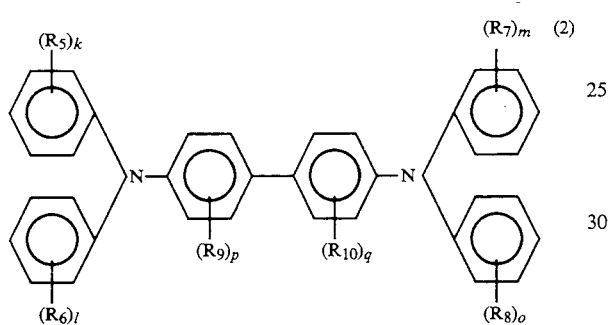

(2)

wherein $R_5$, $R_6$, $R_7$, $R_8$, $R_9$ and $R_{10}$ are alkyl groups, alkoxy groups, halogen atoms, aryl groups, nitro groups, cyano groups or alkylamino groups independently of each other, p and q are integers of 0 to 4, and k, l, m and o are integers of 0 to 5,

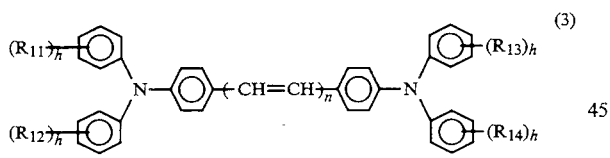

(3)

wherein $R_{11}$, $R_{12}$, $R_{13}$ and $R_{14}$ are hydrogen atoms, alkyl groups or alkoxy groups, and n and h are integers of 1 to 3,

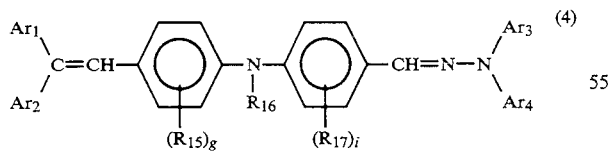

(4)

wherein $R_{15}$ and $R_{17}$ are alkyl groups, alkoxy groups or halogen atoms, g and i are integers of 0 to 4, $R_{16}$ is a hydrogen atom, an alkyl group which may have a substituent, an aralkyl group, an aryl group, or a heterocyclic group, $Ar_1$ and $Ar_2$ are alkyl groups, aralkyl groups, arayl groups or heterocyclic groups which may have substituents but $Ar_1$ and $Ar_2$ may be coupled together to form a ring except when $Ar_1$ and $Ar_2$ are hydrogen atoms simultaneously, and $Ar_3$ and $Ar_4$ are alkyl groups, aralkyl groups, aryl groups or heterocyclic rings which may have substituents but $Ar_3$ and $Ar_4$ may be coupled together to form a ring,

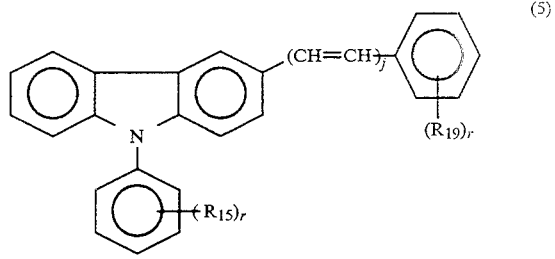

(5)

wherein $R_{15}$ and $R_{19}$ are alkyl groups or an alkoxy groups, and j and r are integers of 0 to 3,

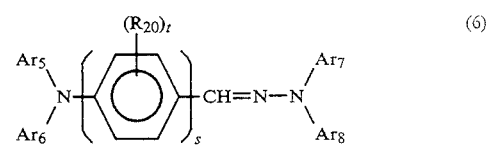

(6)

wherein $R_{20}$ is an alkyl group or an alkoxy group, $Ar_5$, $A_6$, $Ar_7$ and $Ar_8$ are hydrogen atoms, alkyl groups, alkoxy groups, aralkyl groups or aryl groups which may have a substituent, and s is an integer of 1 to 2, and t is an integer of 0 to 2,

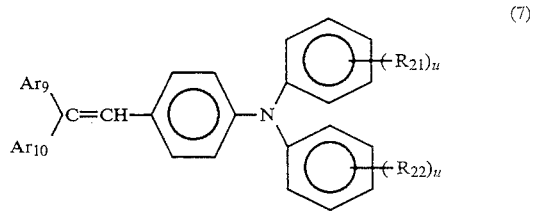

(7)

wherein $R_{21}$ and $R_{22}$ are alkyl groups or alkoxy groups, u is an integer of 0 to 2, and $Ar_9$ and $Ar_{10}$ are aryl groups which may have a substituent,

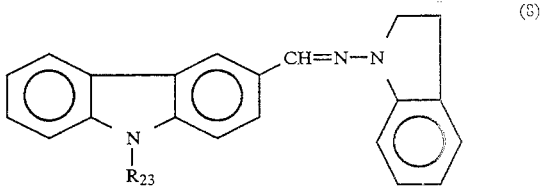

(8)

wherein $R_{23}$ is an alkyl group or an aryl group,

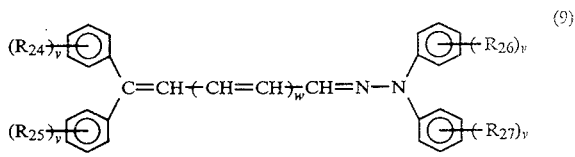

(9)

wherein $R_{24}$, $R_{25}$, $R_{26}$ and $R_{27}$ are alkyl groups or alkoxy groups, and v and w are integers of 0 to 3,

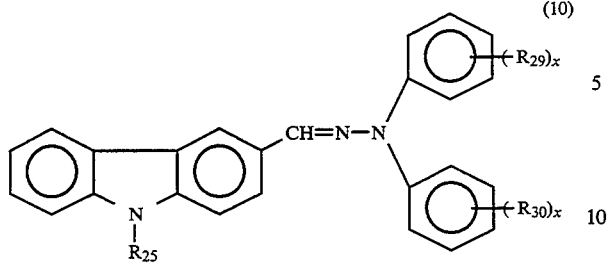
(10)

wherein $R_{25}$ is an alkyl group or an aryl group, $R_{29}$ and $R_{30}$ are alkyl groups or alkoxy groups independently from each other, and x is an integer of 0 to 3,

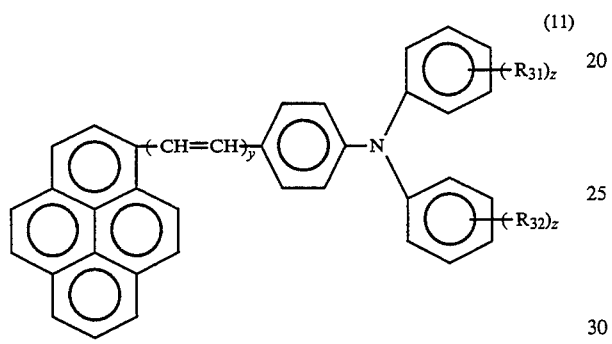
(11)

wherein $R_{31}$ and $R_{32}$ are alkyl groups or alkoxy groups, and y and z are integers of 0 to 3.

32. An electrophotographic photosensitive material comprising an electrically conductive substrate on which is provided a laminated photosensitive layer comprising
a charge generating layer containing a charge generating agent and a binder,
an electron transporting layer containing 10 to 100 parts by weight of a diphenoquinone electron-transporting agent of the formula (1), 10 to 100 parts by weight of a positive hole transporting agent which is at least one member selected from the formulas (2) to (11), and 100 parts by weight of binder,
wherein the diphenoquinone is in an amount of 20 to 80% by weight based on the amount of the diphenoquinone and the positive hole transporting agent.

33. An electrophotographic photosensitive material comprising an electrically conductive substrate on which is provided a laminated photosensitive layer comprising
a charge generating layer comprising a charge generating agent and a binder,
an electron transporting layer containing 10 to 100 parts by weight of a diphenoquinone electron-transporting agent of the formula (1) and 100 parts by weight of a binder, and
a positive hole-transporting layer containing 10 to 100 parts by weight of a positive hole transporting agent which is at least one member selected from the formulas (2) to (11) and 100 parts by weight of binder.

34. A photosensitive material for electrophotography comprising an organic photosensitive layer containing
1 to 20 parts by weight of a charge-generating agent,
10 to 100 parts by weight of a diphenoquinone electron-transporting agent, 10 to 100 parts by weight of a positive hole-transporting agent and 100 parts by weight of a binder,
wherein the diphenoquinone is represented by the following formulas (12), (13) and (14):

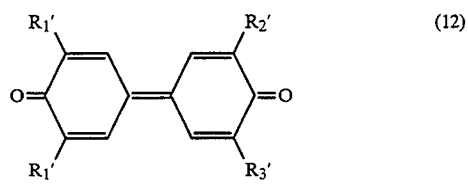
(12)

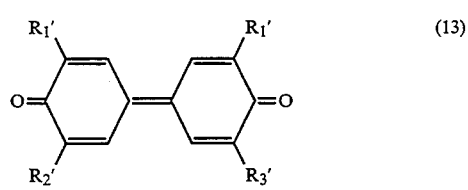
(13)

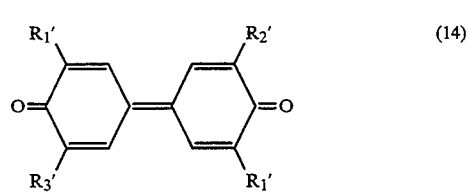
(14)

wherein $R'$ is an alkyl group or an alkoxy group, $R_2'$ is a secondary or tertiary alkyl group, $R_3'$ is an aryl or an alkyl group, and $R_1'$, $R_2'$ and $R_3'$ are different from each other, and
wherein the diphenoquinone is in an amount of 20 to 80% by weight based on the amount of the diphenoquinone and the positive hole-transporting agent.

35. An organic photosensitive material according to claim 34 containing a charge transporting material which consists essentially of the diphenoquinone electron-transporting agent and the positive hole-transporting agent.

36. A photosensitive material for electrophotography comprising an electrically conducting substrate on which is provided a photosensitive layer containing 1 to 20 parts by weight of a charge-generating agent, 10 to 100 parts by weight of a diphenoquinone electron-transporting agent, 10 to 100 parts by weight of a positive hole-transporting agent and 100 parts by weight of a binder,
wherein the diphenoquinone is represented by the following formulas (12), (13) and (14):

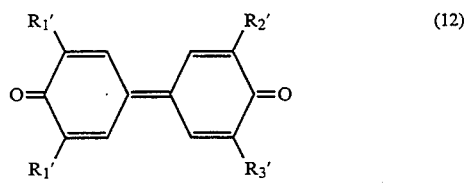
(12)

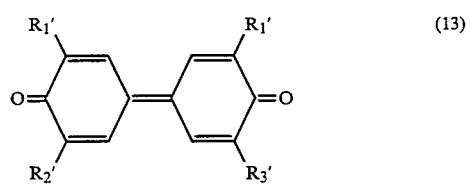
(13)

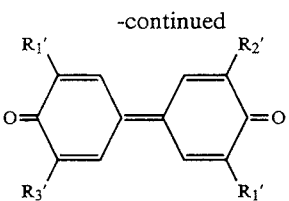

(14)

wherein R' is an alkyl group or an alkoxy group, $R_2'$ is a secondary or tertiary alkyl group, $R_3'$ is an aryl or an alkyl group, and $R_1'$, $R_2'$ and $R_3'$ are different from each other, and wherein the diphenoquinone is in an amount of 20 to 80% by weight based on the amount of the diphenoquinone and the positive hole-transporting agent, and wherein the positive hole-transporting agent is at least one member selected from the formulas (2) to (11).

37. An organic photosensitive material according to claim 36 containing a charge transporting material which consists essentially of the diphenoquinone electron-transporting agent and the positive hole-transporting agent.

* * * * *